(12) United States Patent
Qu et al.

(10) Patent No.: US 8,673,913 B2
(45) Date of Patent: Mar. 18, 2014

(54) SHP-2 PHOSPHATASE INHIBITOR

(75) Inventors: Cheng-Kui Qu, Solon, OH (US); Wen-Mei Yu, Solon, OH (US); Olgun Guvench, Portland, ME (US); Alexander D. Mackerell, Jr., Baltimore, MD (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 12/946,480

(22) Filed: Nov. 15, 2010

(65) Prior Publication Data

US 2011/0257184 A1     Oct. 20, 2011

Related U.S. Application Data

(60) Provisional application No. 61/261,036, filed on Nov. 13, 2009.

(51) Int. Cl.
*A01N 43/64* (2006.01)
*A61K 31/53* (2006.01)

(52) U.S. Cl.
USPC .......................................... 514/243

(58) Field of Classification Search
None
See application file for complete search history.

(56) References Cited

FOREIGN PATENT DOCUMENTS

WO    WO 2007/008541    *    1/2007

OTHER PUBLICATIONS

Tartaglia et al. SHP-2 and myeloid malignancies. Current Opinion in Hematology, 2004, 11: 44-50.*
Chen, Liwei, et al., "Discovery of a Novel Shp2 Protein Tyrosine Phosphatase Inhibitor", *Mol Pharmacol* 70:562-570, 2006.
Yu, Wen-Mei, "Identification of Small Molecular Weight Inhibitors of Src Homology 2 Domain-Containing Tyrosine Phosphatase 2 (SHP-2) via in Silico Database Screening Combined with Experimental Assay", *J. Med. Chem.* 2008, 51, 7396-7404.
Zheng, Hong, "SHP-2 tyrosine phosphatase in human disease", Int J Clin Exp Med 2009 2, 17-25.

* cited by examiner

*Primary Examiner* — Anna Pagonakis
(74) *Attorney, Agent, or Firm* — Tarolli, Sundheim, Covell & Tummino LLP

(57) ABSTRACT

A method of treating SHP-2 phosphatase associated diseases in a subject includes administering a SHP-2 inhibitor to the subject.

5 Claims, 22 Drawing Sheets

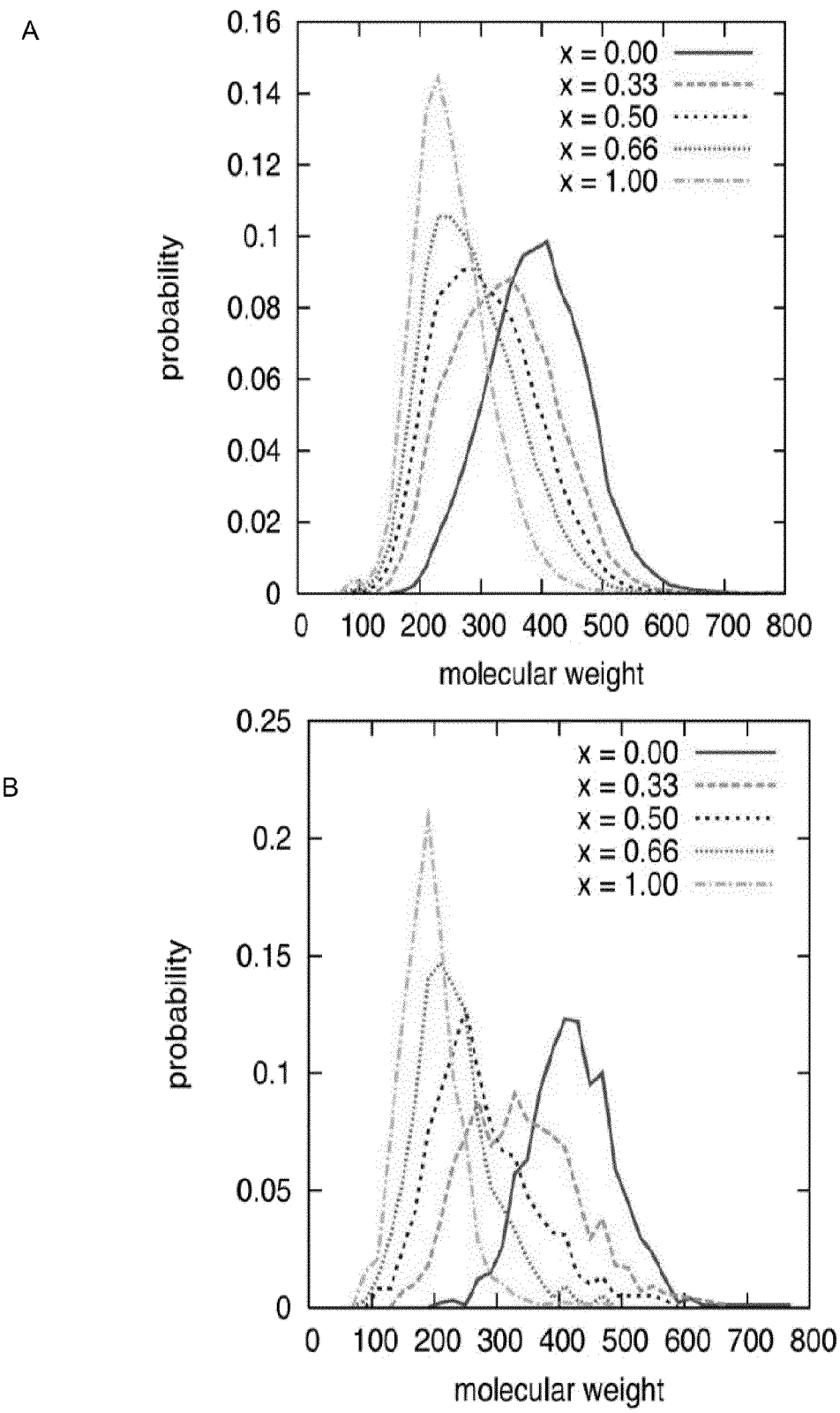
Figs. 2A-B

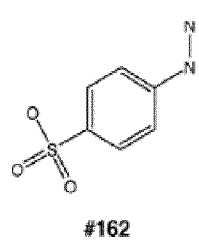
162
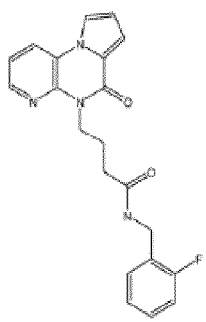
212
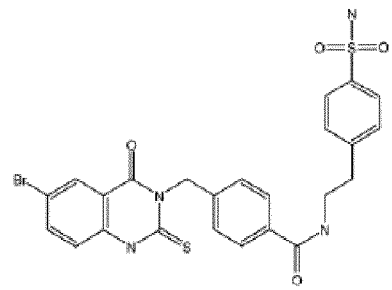
216
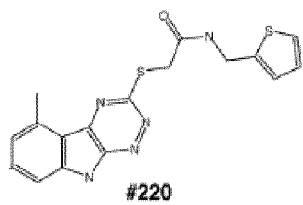
220
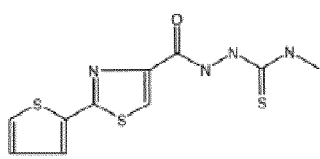
226
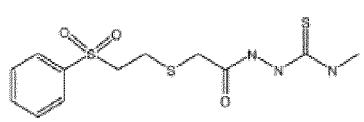
234
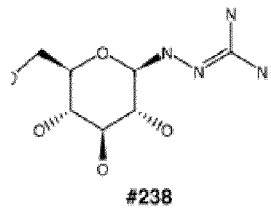
238
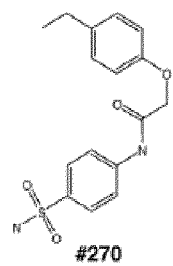
270
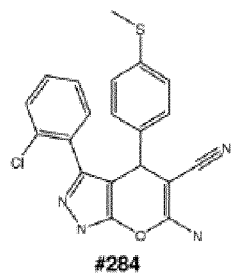
284
Fig. 3B

SHP-2 PHOSPHATASE INHIBITOR

RELATED APPLICATION

This application claims priority from U.S. Provisional Application No. 61/261,036, filed Nov. 13, 2009, the subject matter, which is incorporated herein by reference.

TECHNICAL FIELD

The present application relates to SHP-2 Phosphatase inhibitors and to methods of using such inhibitors for therapeutic applications.

BACKGROUND

Src homology 2 (SH2) domain-containing phosphatase 2 (SHP-2), a ubiquitously expressed SH2 domain containing protein tyrosine phosphatase (PTP), plays a critical role in diverse cell signaling processes. SHP-2 contains two tandem SH2 domains at the N-terminus and a PTP domain at the C-terminus, with flexible polypeptide linker regions connecting the three domains. The 2.0 Å X-ray crystal structure of the self-inhibited form of SHP-2 reveals the formation of an intramolecular protein-protein interface between the N-terminal SH2 (N—SH2) domain and the PTP domain. This self-interaction is characterized by the binding of a loop on the backside of the N—SH2 domain to the catalytic pocket of the phosphatase domain, thereby blocking substrate access to the catalytic site. Numerous inter-domain hydrogen bonds exist in this conformation; some of them are direct and some are bridged by water molecules.

Polypeptide ligands with phosphotyrosine (pY) residues activate SHP-2 by binding the tandem SH2 domains, which disrupts the N—SH2:PTP interface leading to exposure of the PTP catalytic site. Thus, the recognition of pY-peptides by the SH2 domains is normally coupled with the activation of SHP2 phosphatase capability. In most circumstances, SHP-2 plays an overall positive role in transducing signals initiated from growth factors/cytokines and extracellular matrix proteins. Despite extensive studies over the past decade, the signaling mechanisms of SHP-2 are still not well understood. For example, the molecular basis for the positive role of its catalytic activity in the Erk pathway remains elusive. Part of the reason for this is the lack of SHP-2 specific inhibitors that can be used as research tools to probe SHP-2 signaling.

Consistent with its overall positive role in cell signaling, genetic lesions in the SHP-2 gene (PTPN11) that cause hyperactivation of its catalytic activity have been identified in the developmental disorder Noonan syndrome and various childhood leukemias, including juvenile myelomonocytic leukemia (JMML), B cell acute lymphoblastic leukemia, and acute myeloid leukemia. Fifty percent of the patients with Noonan syndrome, 35% of JMML, and 6% of B cell-ALL cases harbor SHP-2 mutations. Moreover, activating mutations of SHP-2 have also been identified in sporadic solid tumors. The SHP-2 mutations found in these diseases are associated with changes in amino acids located at the interface formed by the N—SH2 and PTP domains in the self-inhibited SHP-2 conformation. Therefore, it is thought that these mutations cause a decrease in the affinity of the binding between the N—SH2 and PTP domains, leading to the gain of function (GOF) by allowing access to the phosphatase catalytic site on the enzyme. Remarkably, the SHP-2 mutations appear to play a causal role in the development of these diseases since SHP-2 mutations and other JMML-associated Ras or Neurofibromatosis 1 mutations are mutually exclusive. Furthermore, recent studies have shown that single SHP-2 GOF mutations are sufficient to induce cytokine hypersensitivity in hematopoietic progenitor cells and Noonan syndrome and JMML-like myeloproliferative disease in mice.

SUMMARY

This application relates to compounds or therapeutic agents that can be used as selective inhibitors of Src homology 2-containing tyrosine phosphatase (SHP-2), such as mammalian (e.g., human) SHP-2. The compounds described herein are effective in inhibiting SHP-2 mediated cellular functions and inhibited at least about 50% of SHP-2 catalytic activity at 100 µM in the experimental screening.

In an aspect of the application, the therapeutic agent can include at least one compound having the following general formula:

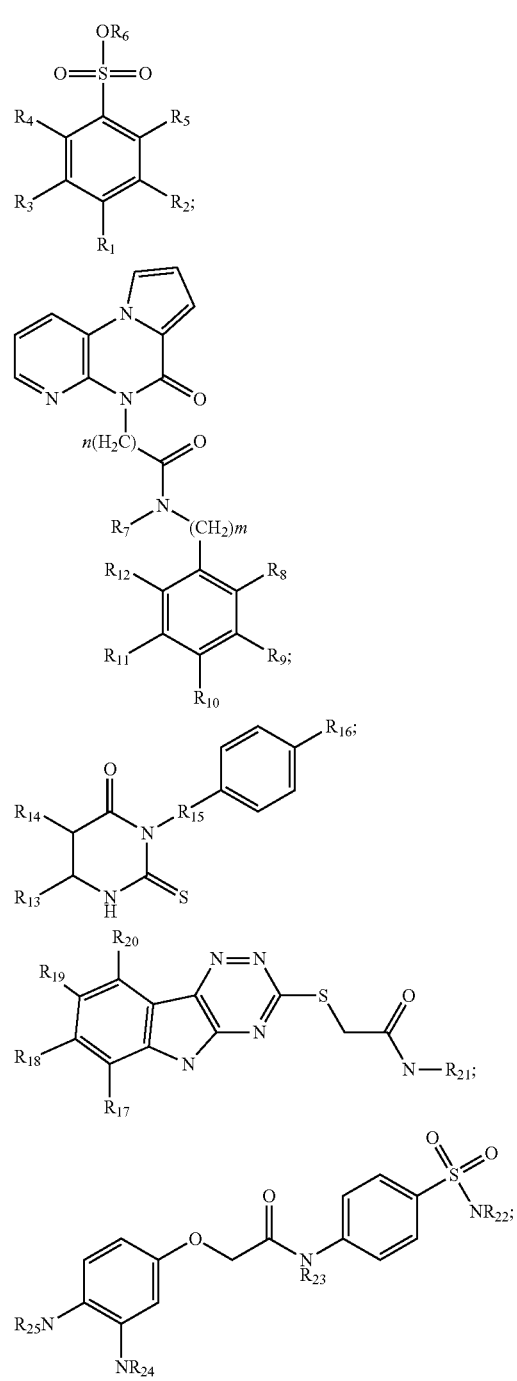

-continued

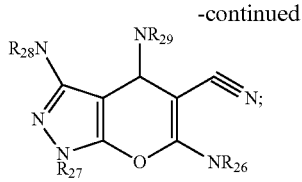

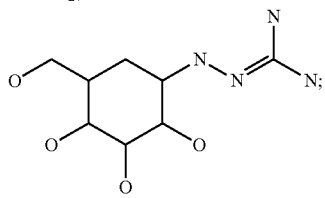

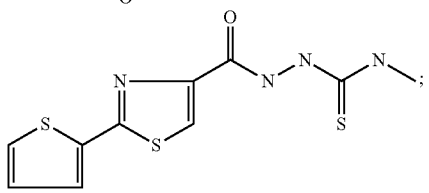

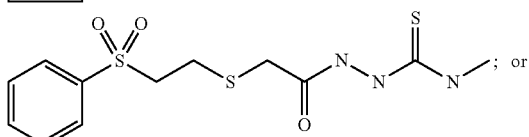

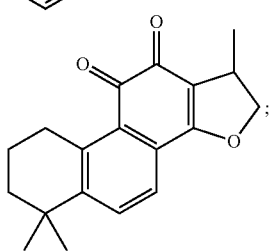

wherein n=1-4; m=1-4, and wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{29}$ can reach individually represent a substituent selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, substituted aryl, substituted alkyl, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), combinations thereof; and a pharmaceutically acceptable salt thereof. In an aspect of the application, the compound can have a molecular weight of less than 500 daltons.

In another aspect of the application, the therapeutic agent can include at least one compound having the general formula:

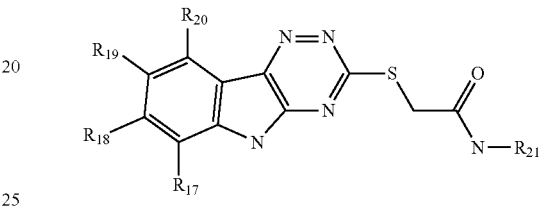

wherein $R_{17}$, $R_{18}$, $R_{19}$, $R_{20}$, $R_{21}$, each individually represent a substituent selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl, arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), phosphino (—PH$_2$), combinations thereof; and a pharmaceutically acceptable salt thereof, and wherein the at least one compound has a molecular weight less than about 500 daltons.

In a further aspect of the application, $R_{17}$, $R_{18}$, $R_{19}$, and $R_{20}$ can each represent H or a lower alkyl group and $R_{21}$ can be selected from the group consisting of H, F, Cl, Br, I, a lower alkyl group, an alkylene group, an alkenyl group, an alkynyl group, an alkoxy group, an aryl group, an aryloxy group, an alkaryl group, and an aralkyl group.

In a still further aspect the compound can be selected from the group consisting of:

220

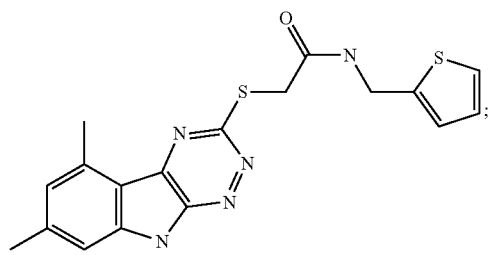

220-247

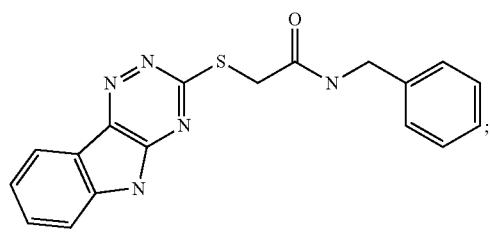

220-248

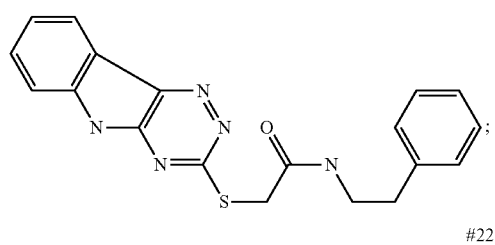

220-323

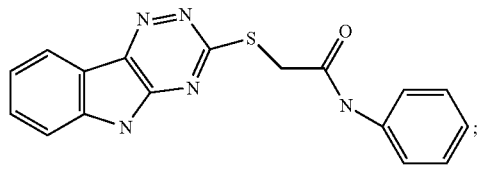

220-324

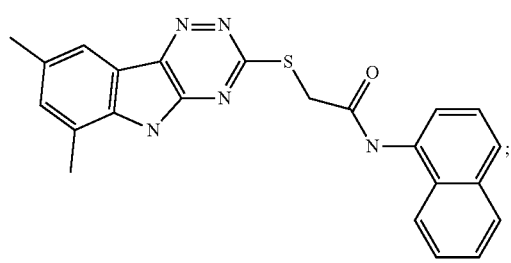

220-325

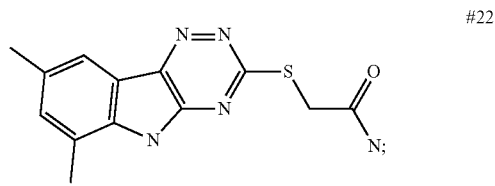

220-326

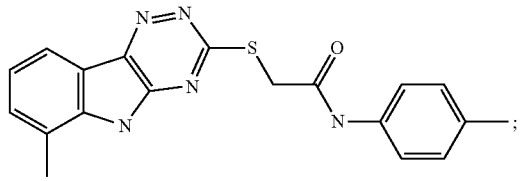

220-328

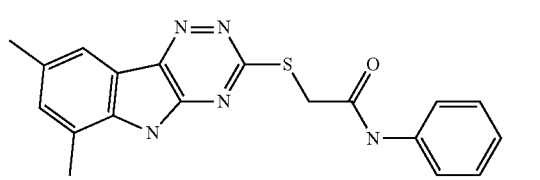

and a pharmaceutically acceptable salt thereof.

In another aspect, the therapeutic agent for selectively inhibiting SHP-2 phosphatases associated diseases and conditions in humans can include at least one compound having the general formula:

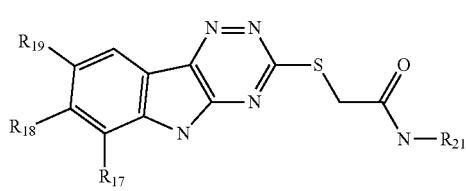

wherein $R_{17}$, $R_{18}$, $R_{19}$, and $R_{21}$ can each individually represent a substituent selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, $(CH_2)_n$ OR' (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, C=O, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, and a pharmaceutically acceptable salt thereof.

In a further aspect of the application, $R_{17}$, $R_{18}$, and $R_{19}$, can each represent H or a lower alkyl group and $R_{21}$ can be selected from the group consisting of H, F, Cl, Br, I, a lower alkyl group, an alkylene group, an alkenyl group, an alkynyl group, an alkoxy group, an aryl group, an aryloxy group, an alkaryl group, and an aralkyl group.

In a still further aspect the compound can be selected from the group consisting of:

220-247

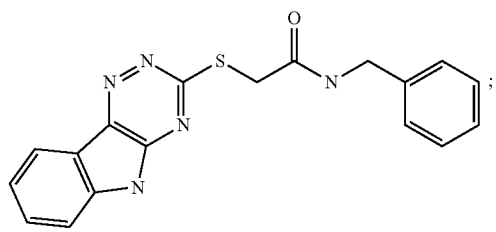

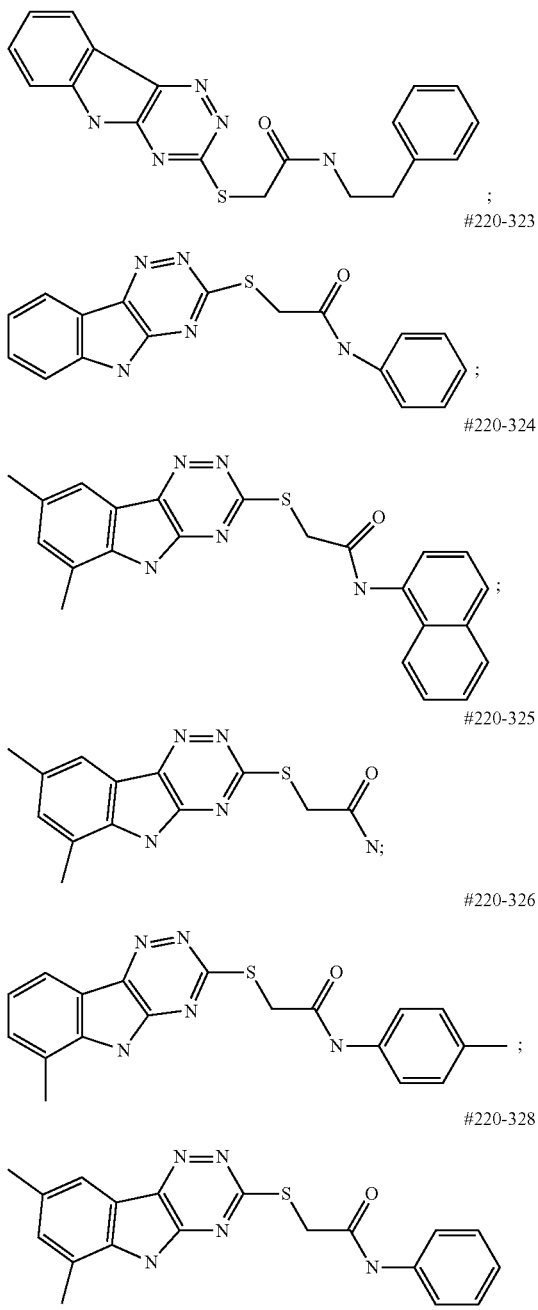

and a pharmaceutically acceptable salt thereof.

In another aspect, an inhibitory amount of the compound can be used as a therapeutic agent for selectively inhibiting SHP-2 phosphatase.

In further aspect, the therapeutic agents described herein can be used in a method for treating Noonan Syndrome in a subject. The method can include administering to the subject a therapeutically effective amount of the therapeutic agent.

In yet another aspect of the application, the compound can be used as a therapeutic agent in a method for treating leukemia. The method can include the step of administering to the subject a therapeutically effective amount of the therapeutic agent.

BRIEF DESCRIPTION OF THE DRAWINGS

FIG. 2 illustrates molecular weight distribution histograms of the top scoring compounds after normalization of docking energies. (A) Distributions of the top 50,000 compounds after primary docking. (B) Distributions of the top 1000 compounds after secondary docking. Scoring is based on the normalized interaction energy IEnorm, which is calculated as IE/Nx, where N is the number of non-hydrogen atoms in each ligand and x is an exponent of N and ranges from 0 (no normalization) to 1 (full normalization).

DETAILED DESCRIPTION

Figure 1:
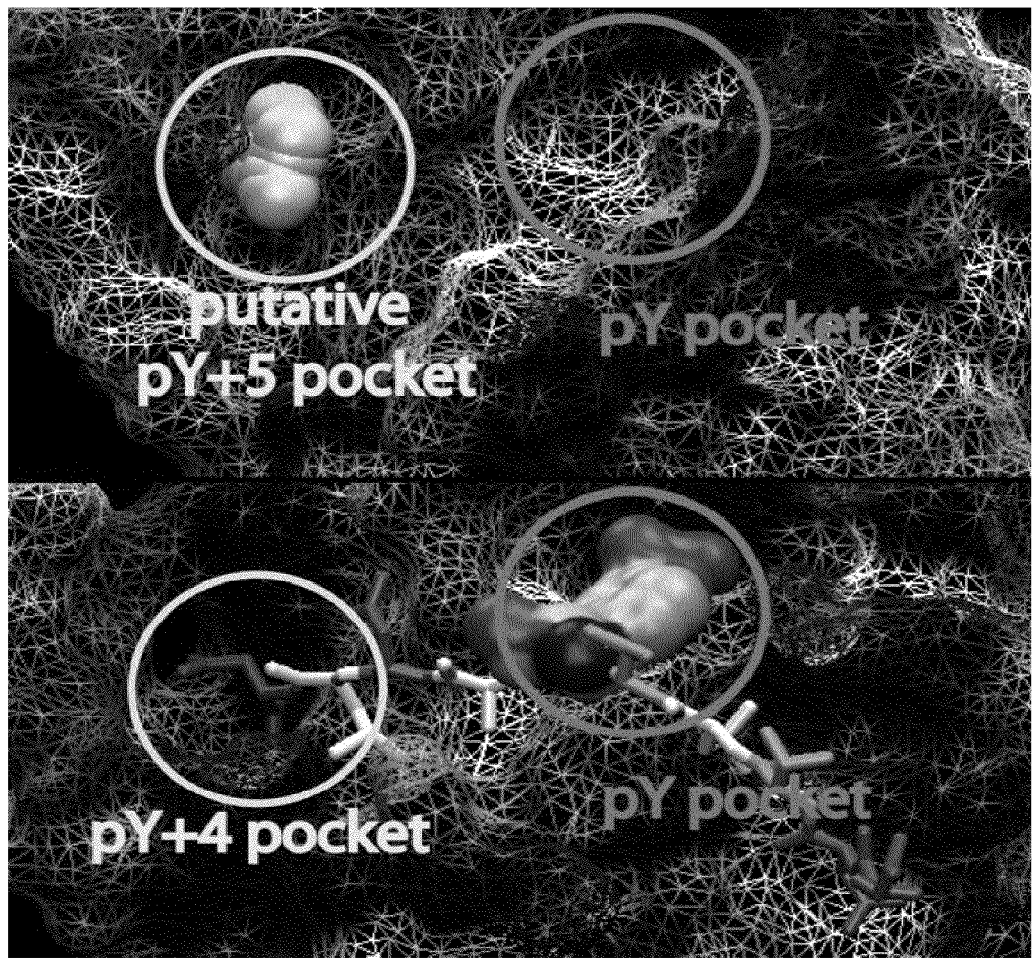
FIG. 1 illustrates the location of the docking site on the SHP-2 catalytic domain. Top: Sphere set (yellow) in the putative pY+5 pocket used for docking to the crystal structure of the SHP-2 PTP domain (wireframe). The locations of the residues used in selecting the sphere set are such that residues 255, 258, and 261 lie to the left of the spheres, 498 is behind the spheres at the base of the pocket, and 503 is to the right of the spheres. Bottom: Crystal structure of the homologous SHP-1 PTP domain and bound pY peptide [PDB ID 1FPR], with the pY residue shown as a molecular surface. Amino acids are colored according to type: Red=acidic, blue=basic, green=polar, white=hydrophobic, cyan=aromatic. Molecular graphics were prepared with VMD.

This application relates to compounds or therapeutic agents that can be used as selective inhibitors of Src homology 2-containing tyrosine phosphatase (SHP-2), such as mammalian (e.g., human) SHP-2. Low molecular weight compounds (e.g., less than about 500 daltons) that selectively inhibit SHP-2 catalytic activity were identified using CADD screening of a virtual database of compounds against the 3D structure of SHP-2 and then further screened using an in vitro phosphatase assay. The compounds described herein are effective in inhibiting SHP-2 mediated cellular functions and inhibited at least about 50% of SHP-2 catalytic activity ($IC_{50}$) at up to about 100 μM (i.e., about 100 μm or less) in the experimental screening.

The therapeutic agent in accordance with the application can include at least one compound have the following general formula:

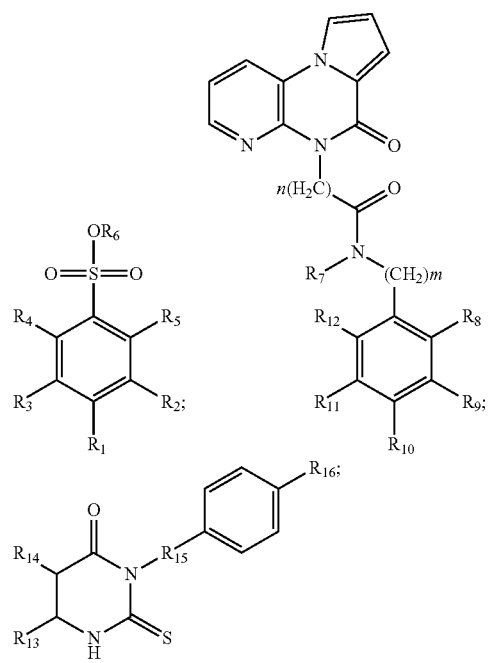

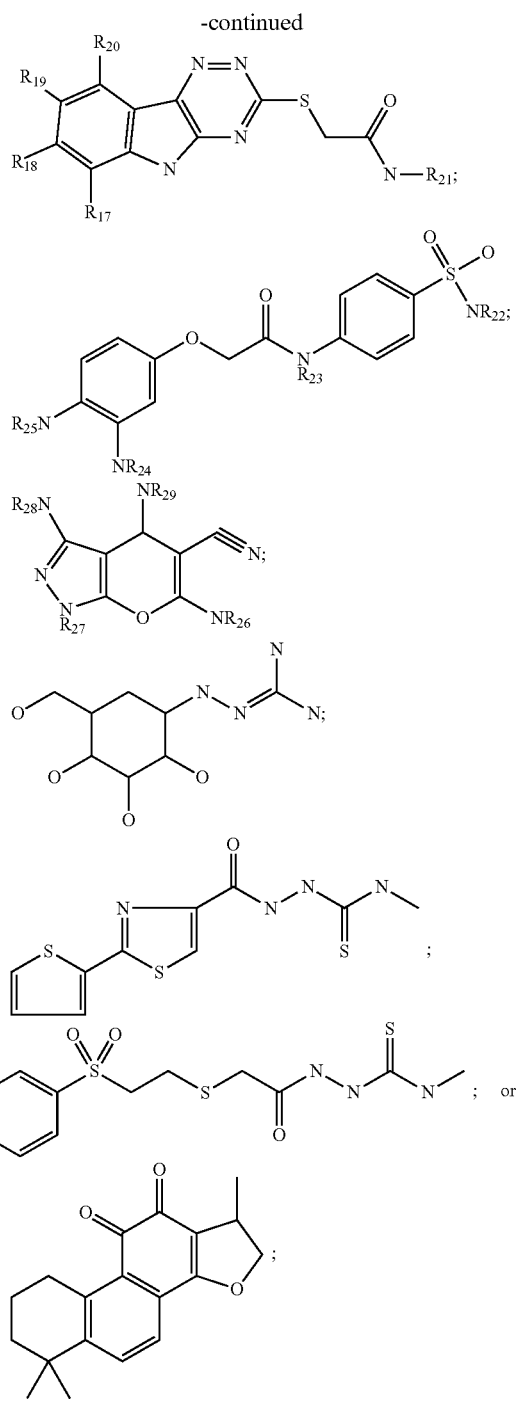

wherein n=1-4; m=1-4, and wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{29}$ can each individually represent a substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, substituted aryl, substituted alkyl, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof; and a pharmaceutically acceptable salt thereof.

The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl"

include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N+C—), cyanato (—O—CN), isocyanato (—ON+C—), isothiocyanato (—S—CN), azido (—N=N+=N—), formyl (—(CO)—H), thioformyl (—(CS)—H), amino (—NH2), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O—)$_2$), phosphinato (—P(O)(O—)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a compound, the term "compound" is intended to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

Some of the compounds disclosed herein may contain one or more asymmetric centers and may thus give rise to enantiomers, diastereomers, and other stereoisomeric forms. The present application is also meant to encompass racemic mixtures, resolved forms and mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "asymmetric center" or "chiral center" refers to a carbon atom to which four different groups are attached.

The term "enantiomer" or "enantiomeric" refers to a molecule that is nonsuperimposeable on its minor image and hence optically active wherein the enantiomer rotates the plane of polarized light in one direction and its minor image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its minor image molecule.

In an embodiment of the application, the therapeutic agent can include at least one compound having the general formula:

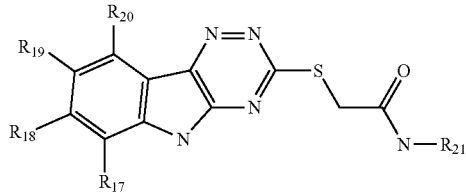

wherein $R_{17}$, $R_{18}$, $R_{19}$, $R_{20}$, and $R_{21}$, each individually represent a substituent selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—O—$N^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl, arylsulfanyl, $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof; and a pharmaceutically acceptable salt thereof, and wherein the at least one compound has a molecular weight less than about 500 daltons.

In another embodiment of the application, $R_{17}$, $R_{18}$, $R_{19}$, and $R_{20}$ can each represent H or a lower alkyl group and $R_{21}$ can be selected from the group consisting of H, F, Cl, Br, I, a lower alkyl group, an alkylene group, an alkenyl group, an alkynyl group, an alkoxy group, an aryl group, an aryloxy group, an alkaryl group, and an aralkyl group.

In a still further embodiment, the compound can be selected from the group consisting of:

220

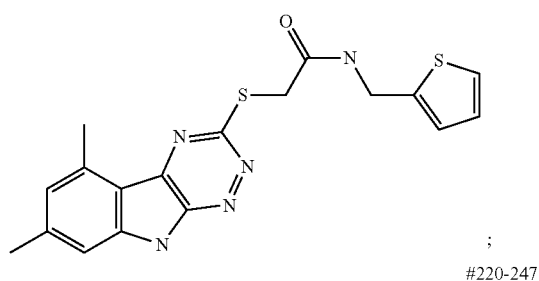

220-247

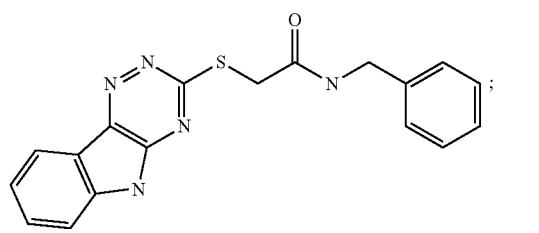

220-248

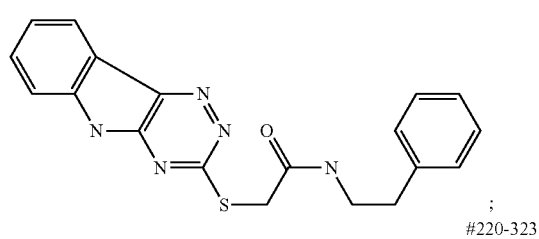

220-323

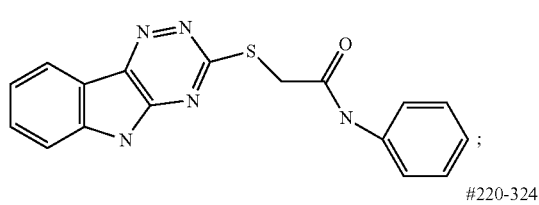

220-324

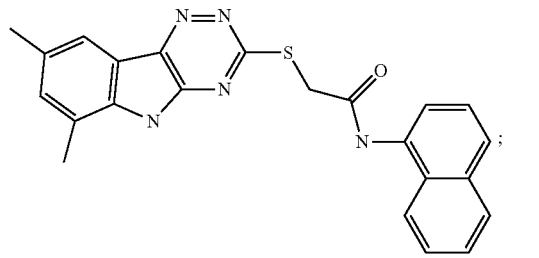

220-325

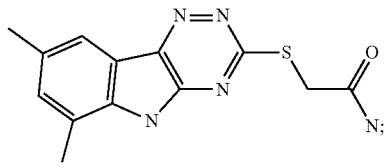

220-326

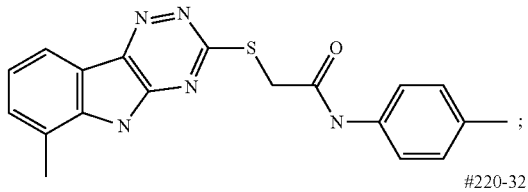

220-328

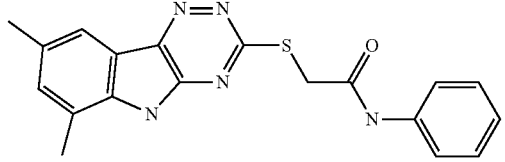

and a pharmaceutically acceptable salt thereof.

In another embodiment, the therapeutic agent for selectively inhibiting SHP-2 phosphatases associated diseases and conditions in humans can include at least one compound having the general formula:

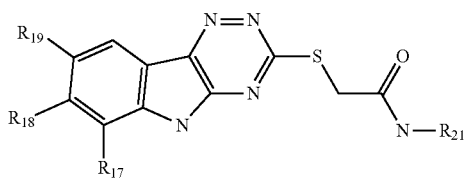

wherein $R_{17}$, $R_{18}$, and $R_{19}$, each individually represent a substituent selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, (CH$_2$)$_n$OR' (wherein n=1, 2, or 3), CF$_3$, CH$_2$—CH$_2$X, O—CH$_2$—CH$_2$X, CH$_2$—CH$_2$—CH$_2$X, O—CH$_2$—CH$_2$X (wherein X=F, Cl, Br, or I), CN, C=O, (C=O)—R', N(R')$_2$, NO$_2$, (C=O)N(R')$_2$, O(CO)R', OR', SR', COOR', $R_{ph}$, CR'=CR'—$R_{ph}$, CR$_2$'—CR$_2$'—$R_{ph}$ (wherein $R_{ph}$ represents an unsubstituted or substituted phenyl group, and a pharmaceutically acceptable salt thereof.

In a further embodiment of the application, $R_{17}$, $R_{18}$, and $R_{19}$, can each represent H or a lower alkyl group and $R_{21}$ can be selected from the group consisting of H, F, Cl, Br, I, a lower alkyl group, an alkylene group, an alkenyl group, an alkynyl group, an alkoxy group, an aryl group, an aryloxy group, an alkaryl group, and an aralkyl group.

In a still further embodiment, the compound can be selected from the group consisting of:

220-247

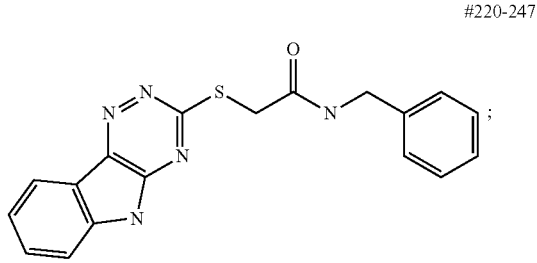

-continued

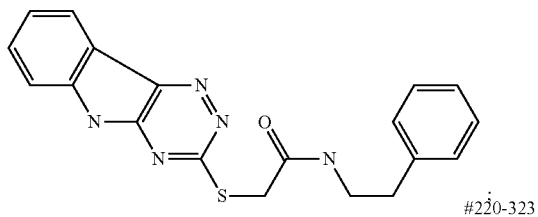
220-248

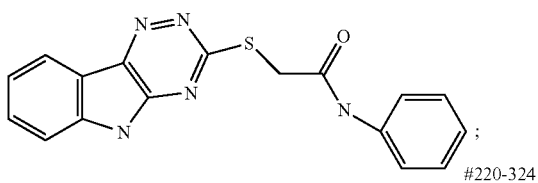
220-323

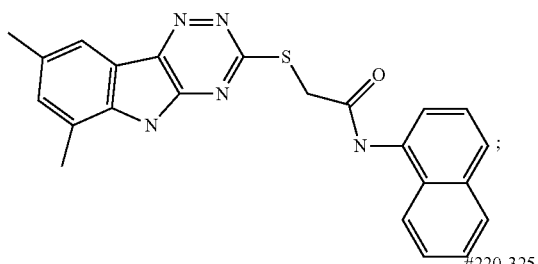
220-324

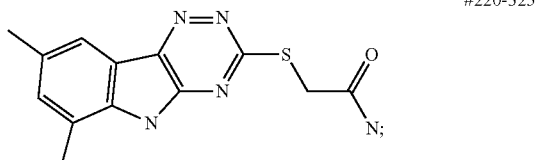
220-325

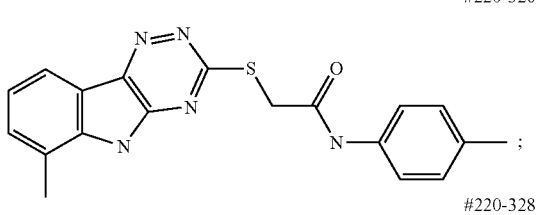
220-326

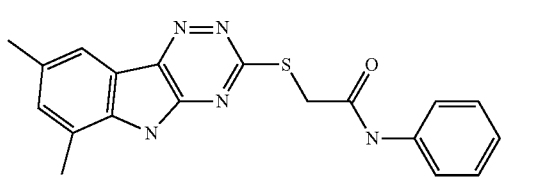
220-328 and a pharmaceutically acceptable salt thereof.

By way of example, the compound can have the following formula:

220-324

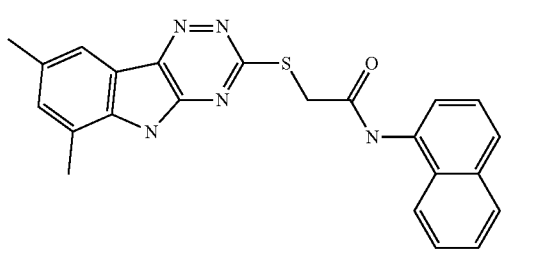

or be a pharmaceutically acceptable salt thereof.

Figure 10:
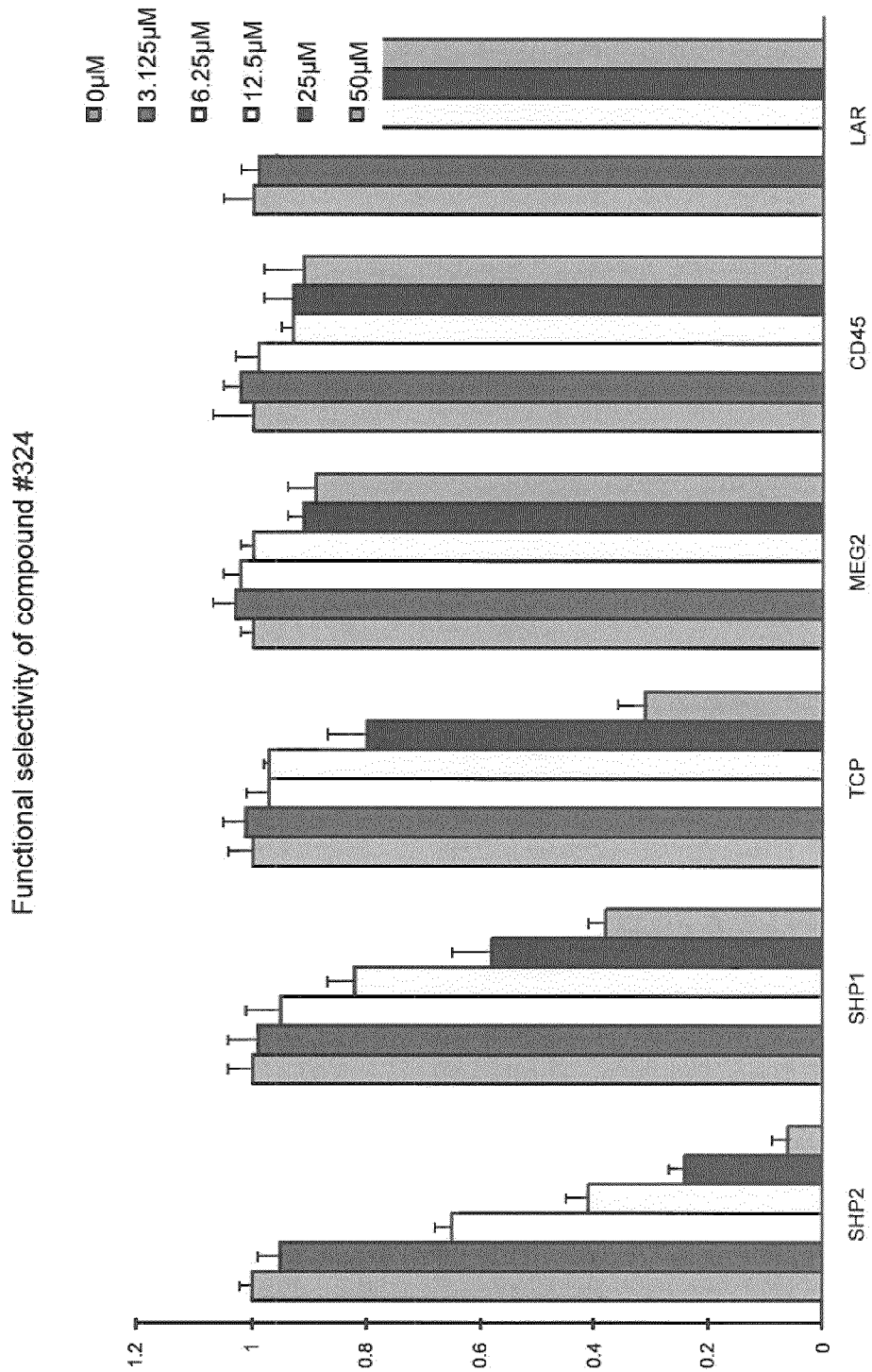
FIG. 10 illustrates functional specificity of active similar compounds. Active similar compounds at the indicated concentrations were subjected to the phosphatase assays using SHP-2, SHP-1, CD45, TC-PTP, PTP-MEG2, and LAR as enzymes. DMSO was used as negative controls. Shown are the results of a representative compound #324.
Figure 11:
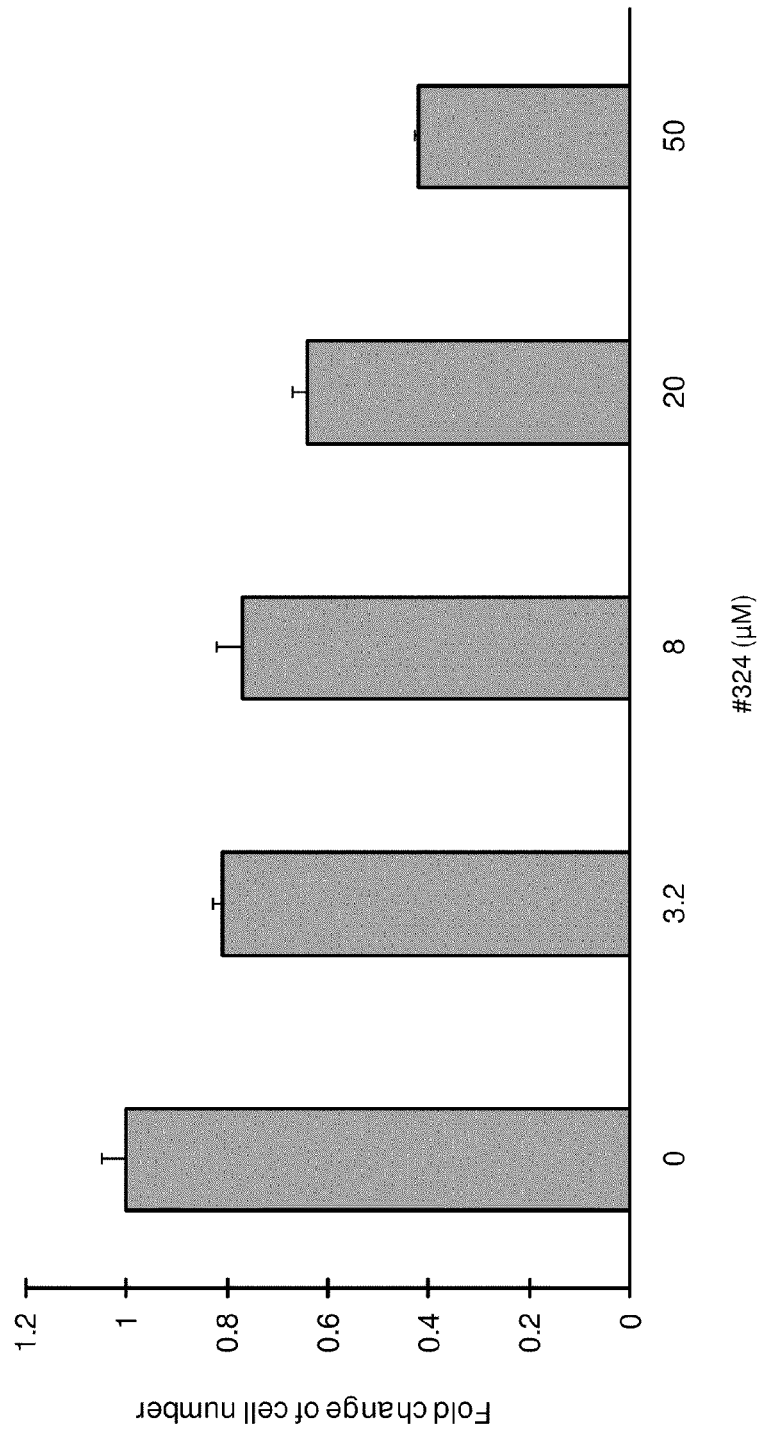
FIG. 11 illustrates inhibition of Ba/F3 cell proliferation by active compounds. Ba/F3 cells were cultured in IL-3 (1 ng/mL) containing medium supplemented with active compounds at the indicated concentrations. DMSO was included at negative controls. Cell numbers were determined 48 hours later using the MTS assay. Shown are the results of a representative compound #324. Note: Both SHP-2 and SHP-1 phophatases are expressed in Ba/F3 cells that depend on IL-3 for growth. While SHP-1 plays a negative role in IL-3 induced cellular responses, SHP-2 plays an overall positive role in cellular response to IL-3. The data that Ba/F3 cell growth in IL-3 containing medium is suppressed by the active compounds we identified suggest that these compounds preferentially inhibit SHP-2 phosphatase.
Figure 12:
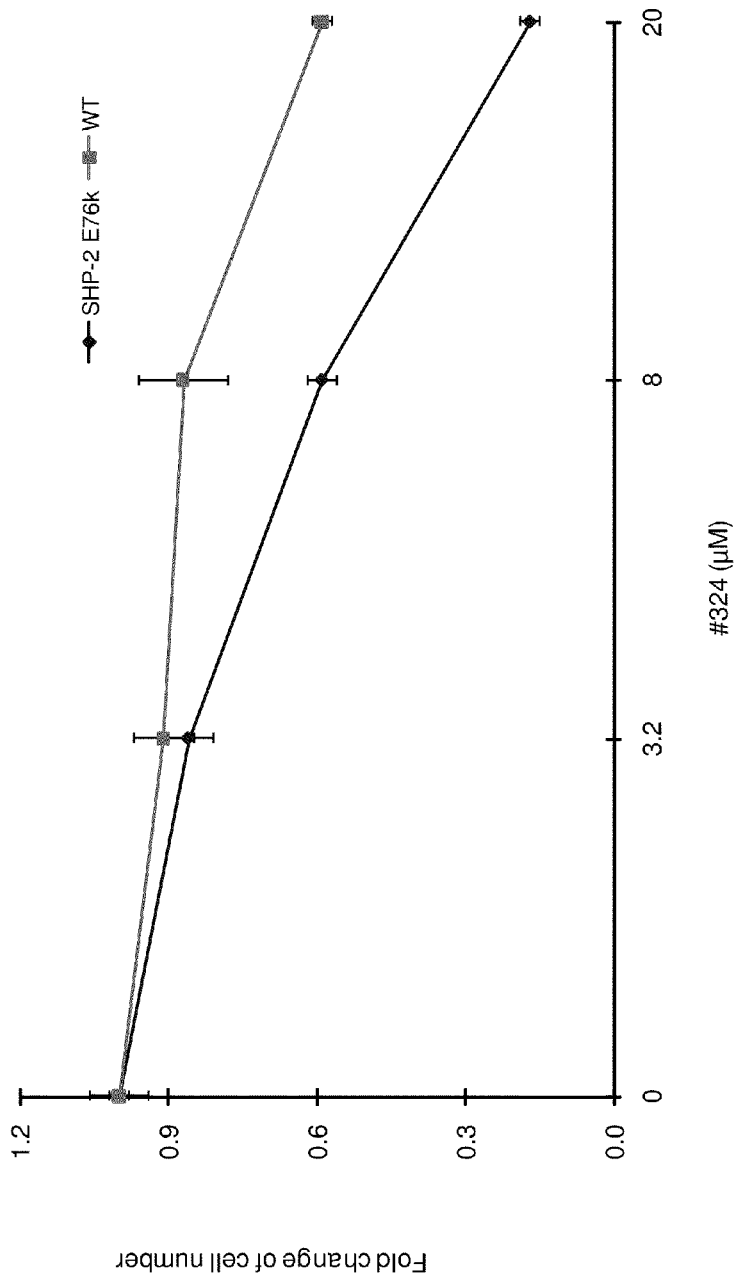
FIG. 12 illustrates fibroblasts with SHP-2 activating mutation E76K are more sensitive to active compounds than wildtype fibroblasts. Mouse embryonic fibroblasts, wildtype and SHP-2 E76K mutant, were cultured in DMEM medium supplemented with active compounds at the indicated concentrations. DMSO was included at negative controls. Cell numbers were determined 48 hours later using the MTS assay. Shown are the results of a representative compound #324. Note: The E76K mutation is the most frequent and the most potent activating mutation of SHP-2 identified in human leukemias and solid tumors.
Figure 13A:
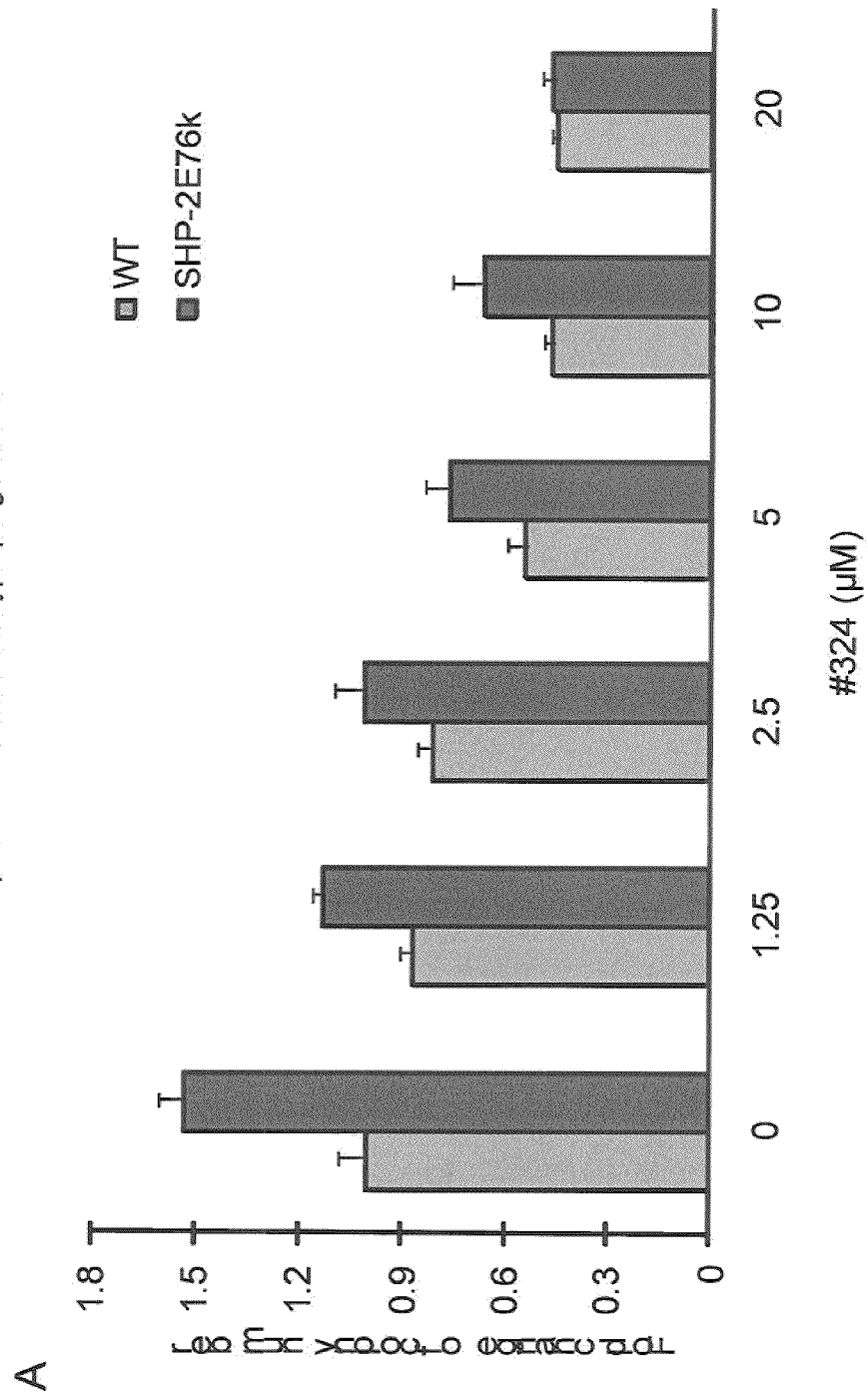
FIG. 13 illustrates A.) Myeloid progenitors with SHP-2 activating mutation E76K are more sensitive to active compounds than wildtype progenitor cells. Bone marrow cells were harvested from wildtype and mutant mice with SHP-2 E76K mutation. IL-3 induced myeloid progenitor cell colony (CFU-GM) formation assays were performed as described in the Examples in the presence of various concentrations of active compounds. Shown are the results of a representative compound #324. B.) Inhibition of growth factor-independent colony formation of myeloid progenitors with SHP-2 activating mutation E76K by active compounds. Bone marrow cells were harvested from wildtype and mutant mice with SHP-2 E76K mutation. The cells were assayed for CFU-GM without cytokines in the presence of various concentrations of active compounds. Shown are the results of a representative compound #324.
Figure 13B:
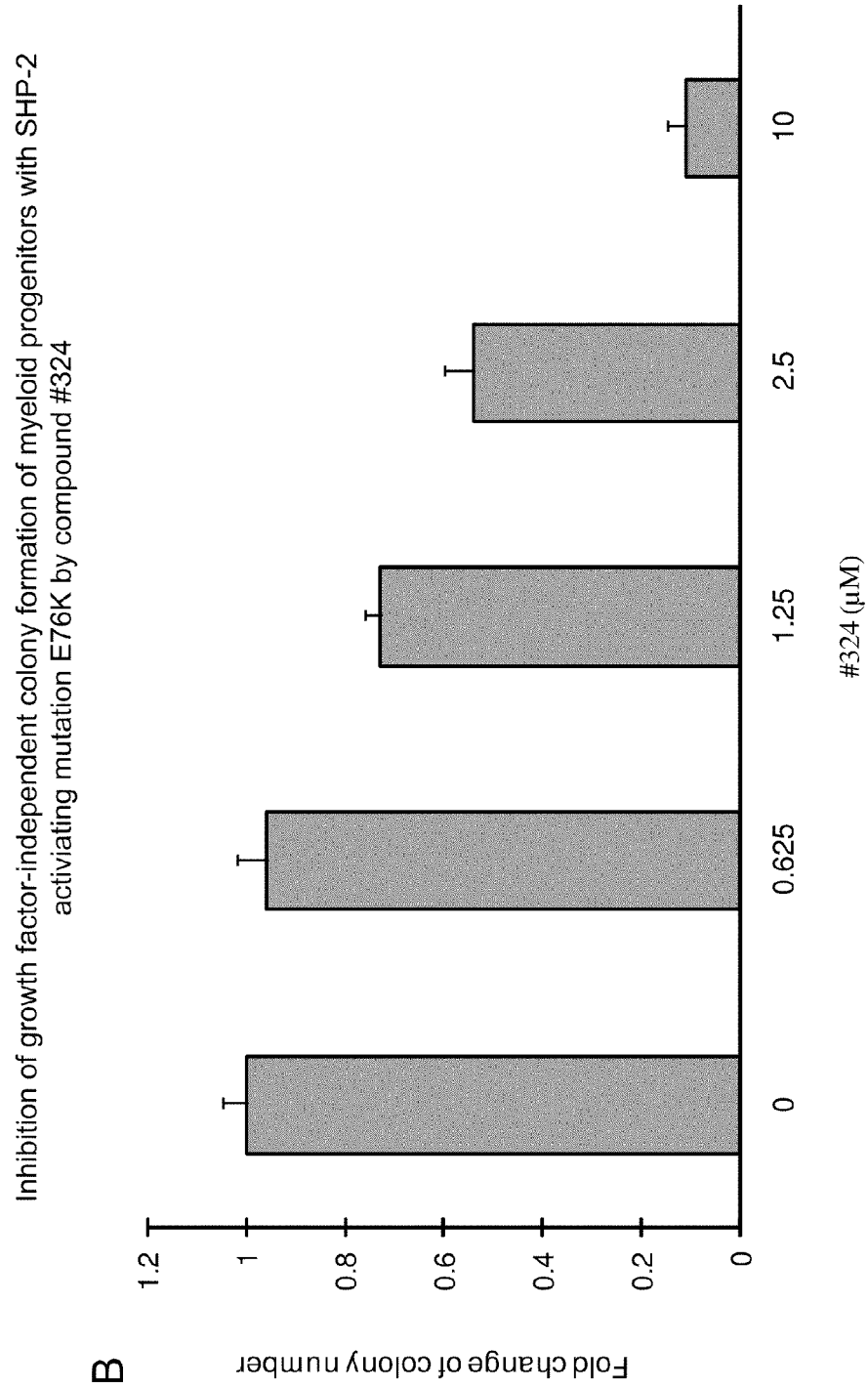
Figure 14A:
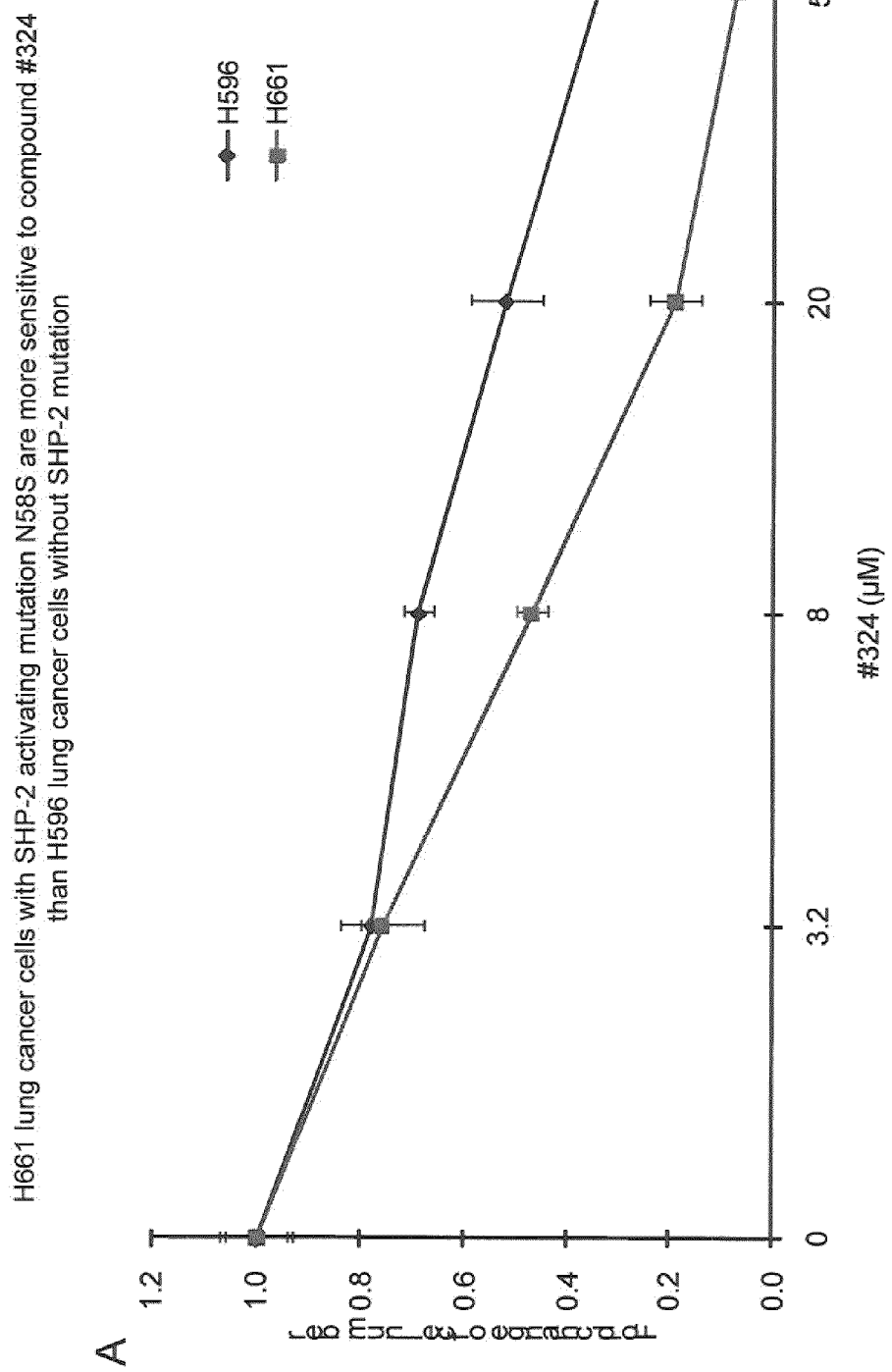
FIG. 14 illustrates A.) H661 lung cancer cells with SHP-2 activating mutation N58S are more sensitive to active compounds than H596 lung cancer cells without SHP-2 mutation. H661 and H596 cells were cultured in DMEM medium supplemented with active compounds at the indicated concentrations. DMSO was included at negative controls. Cell numbers were determined 48 hours later using the MTS assay. Shown are the results of a representative compound #324. B.) H661 lung cancer cells with SHP-2 activating mutation N58S are more sensitive to active compounds than H596 lung cancer cells without SHP-2 mutation. H661 and H596 cells were cultured in DMEM medium supplemented with active compounds (10 μM) for the indicated periods of time. DMSO was included at negative controls. Cell numbers were determined using the MTS assay. Shown are the results of a representative compound #324.
Figure 14B:
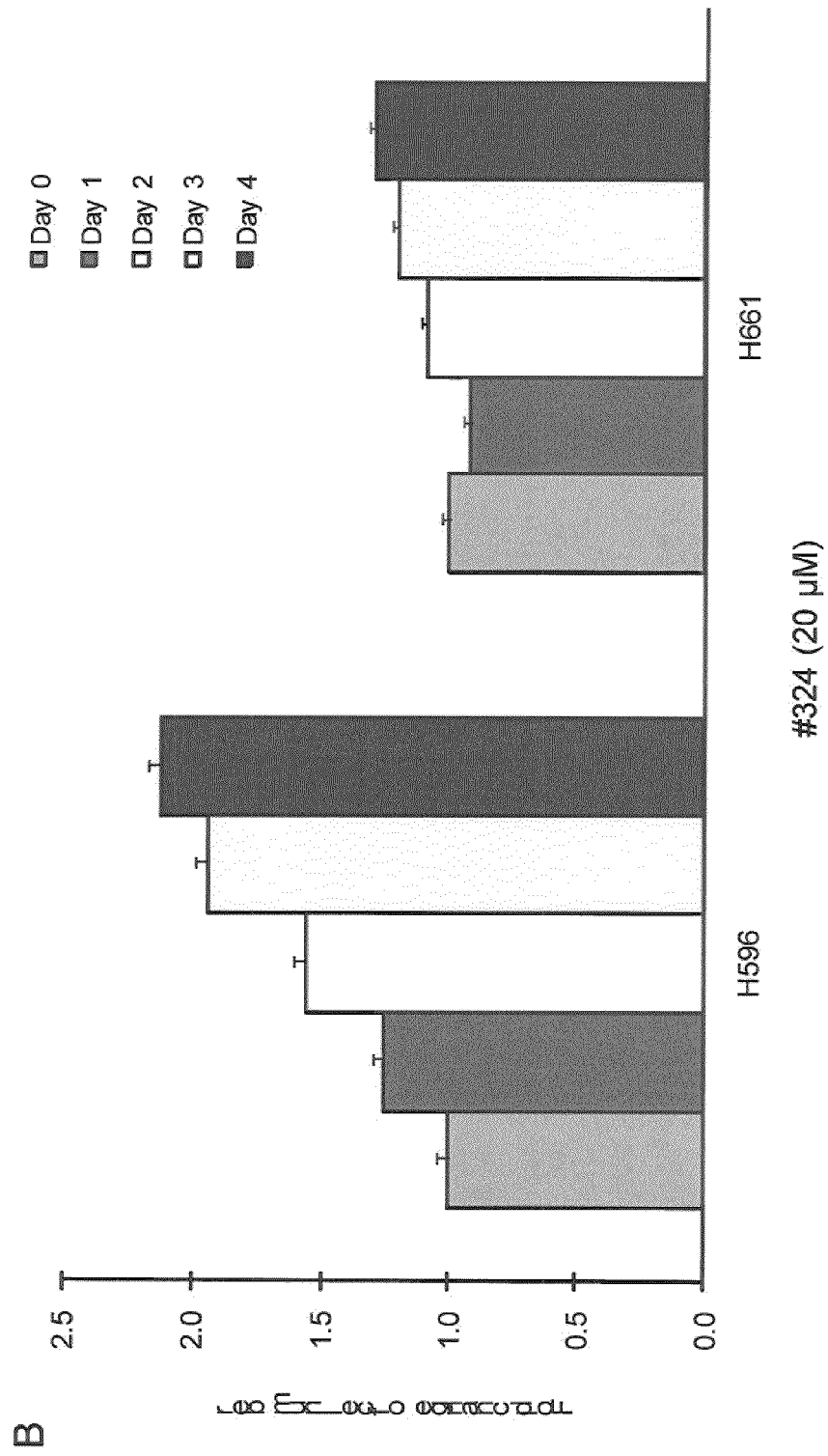

Compound 324 selectively inhibits SHP-2 compared to other PTPases as shown in the Table 1 and FIG. 10. Compound 324 was also found to inhibit SHP-2 mediated proliferative response to IL-3 (Ba/F3 cells) (FIG. 11). Fibroblasts and myeloid progenitors with activating mutation E76K in SH2 were further found to be more sensitive to inhibition with compound 324 than, respectively, wild type fibroblasts and myeloid progenitors (FIGS. 12-14).

| Functional Selectivity of #324 | |
|---|---|
| PTP | $IC_{50}$ (μM) |
| SHP2 | 13.88 |
| SHP1 | 37.69 |
| PTPRC (CD45) | 181.80 |
| LAR | 143.90 |
| MEG2 | 177.40 |
| TC-PTP | 39.94 |

In another embodiment, the compound can have the following formula:

162

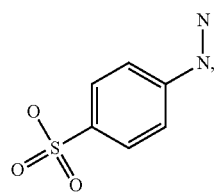

162-286

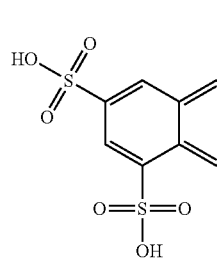

162-287

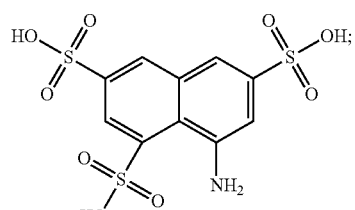

162-288

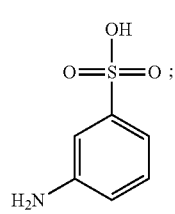

-continued
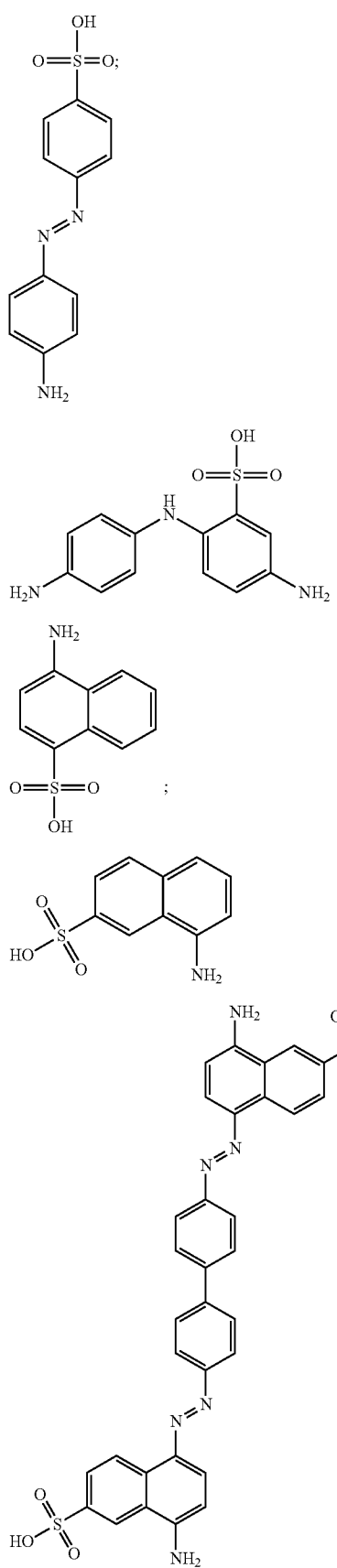
162-289
162-290
162-291
162-293
162-297
-continued
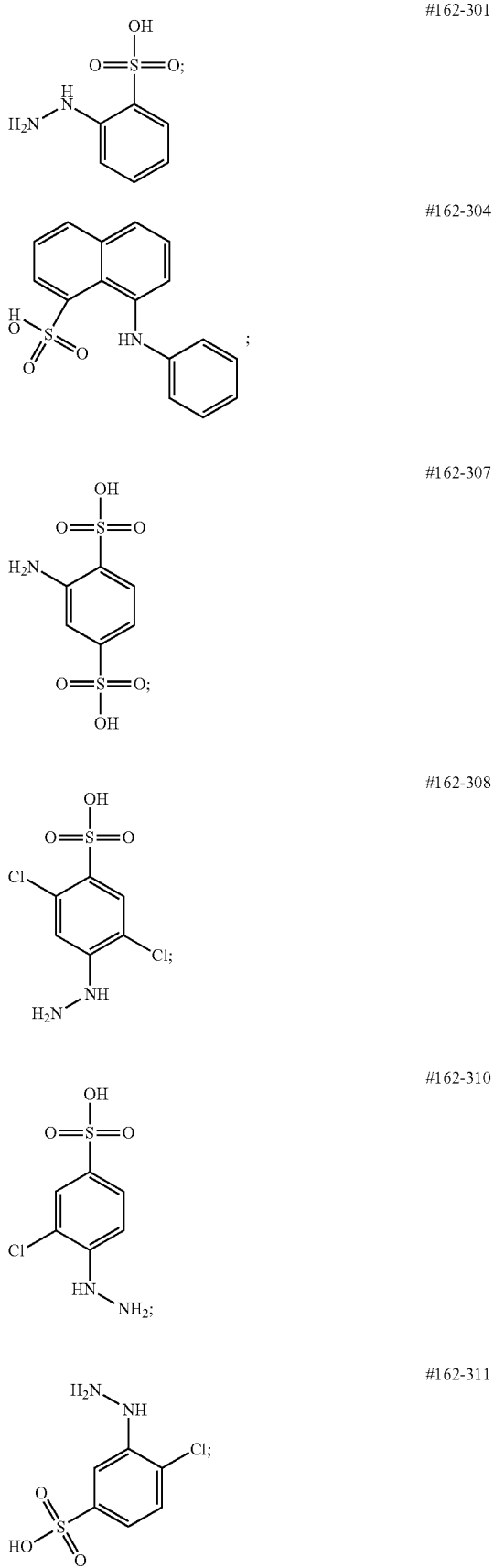
162-301
162-304
162-307
162-308
162-310
162-311

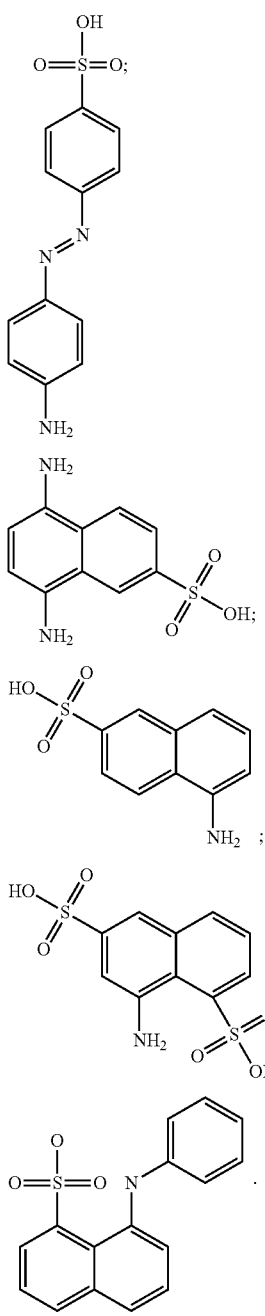
162-312
162-313
162-314
162-317
or
162-322
In yet another embodiment, the compound can have the following formula:
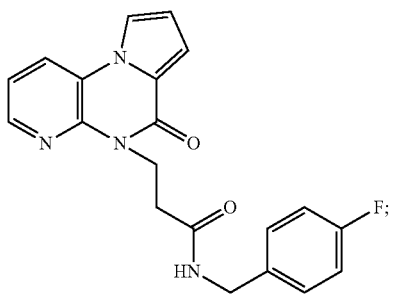
212-339
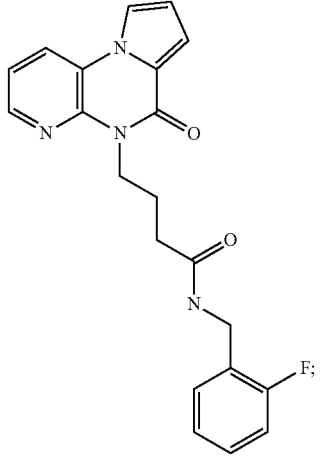
212
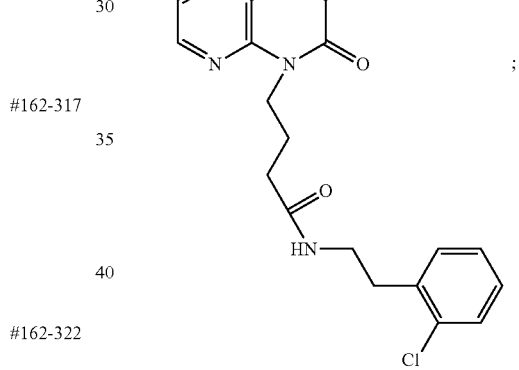
212-337
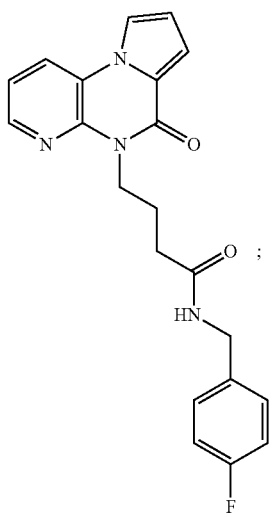
212-338

212-340
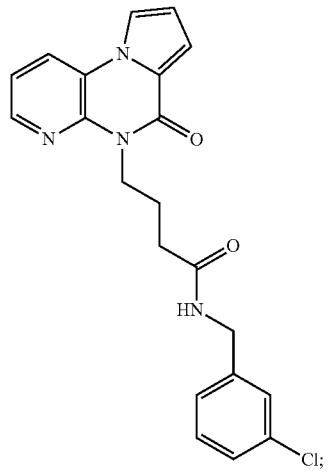
212-343
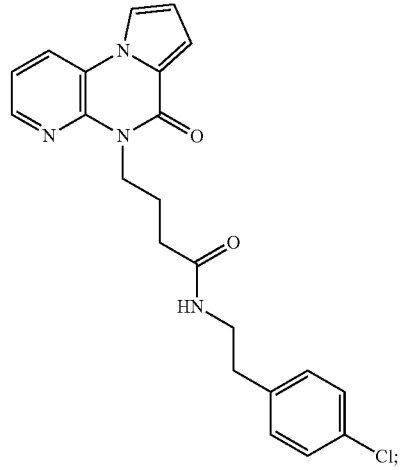
212-341
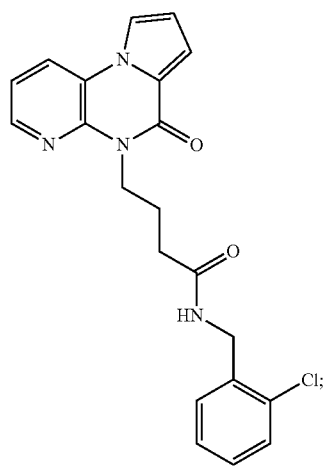
212-344
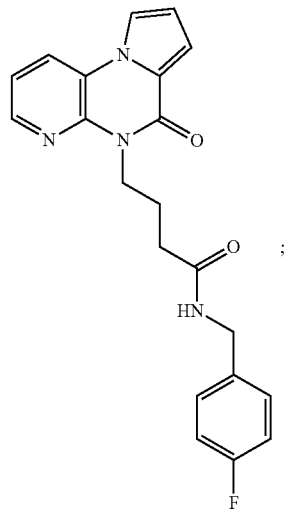
212-342
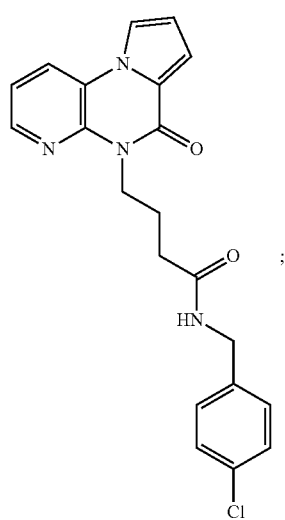
212-345
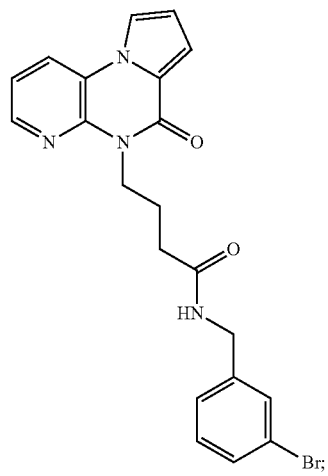

212-346
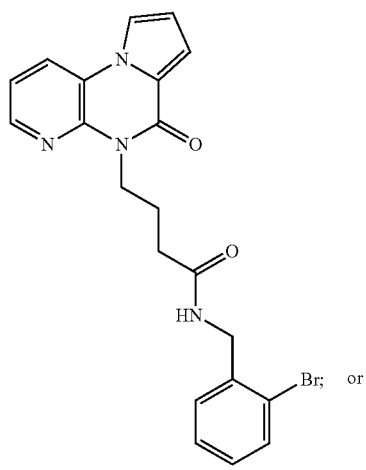
Br; or
212-348
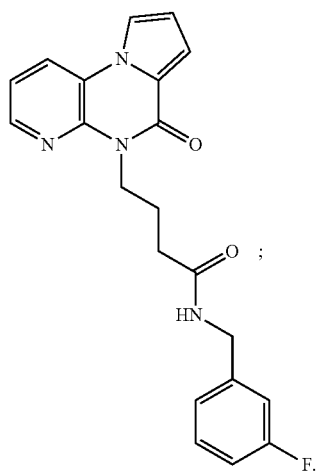
In a further embodiment, the compound can have the following formulas:
216
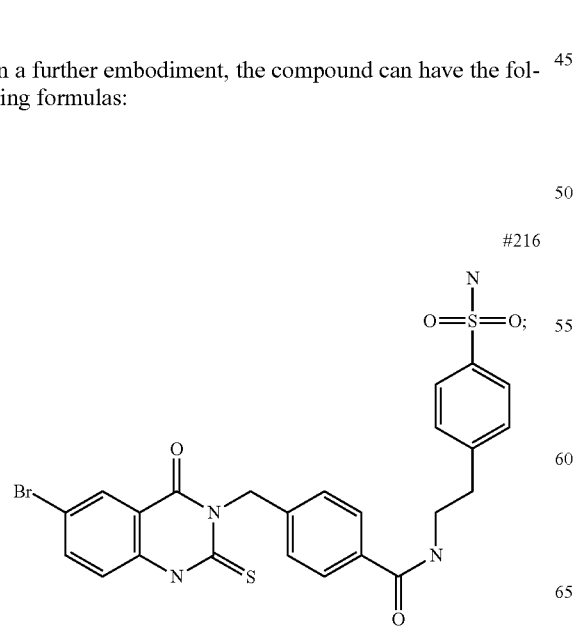
216-255
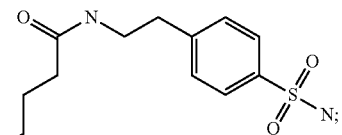
216-258
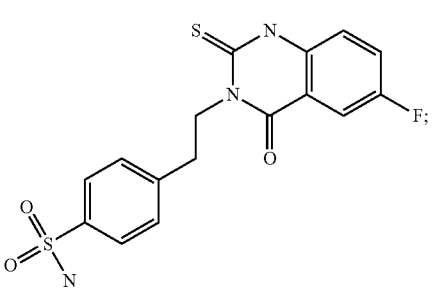
216-259
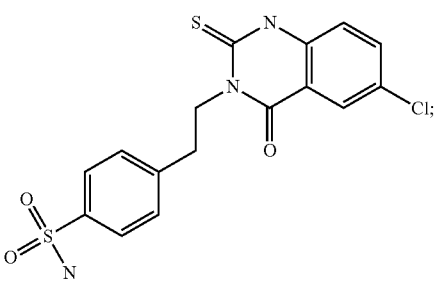
216-262
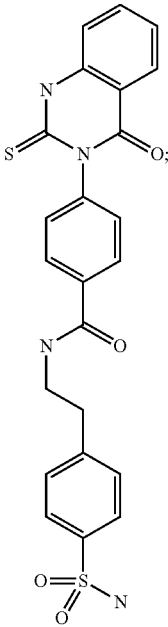

-continued
216-264
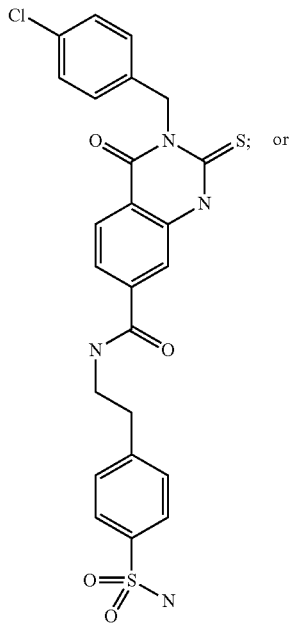
In a still further embodiment, the compound can have the following formula:
226
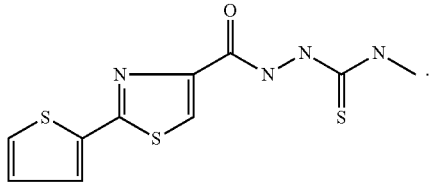
In another embodiment, the compound can have the following formula:
234
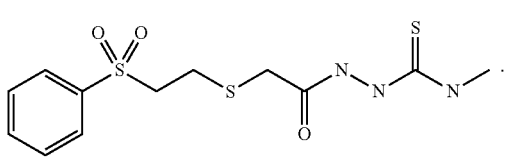
In yet another embodiment, the compound can have the formula:
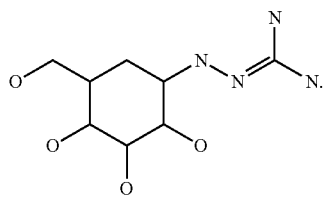
In still yet another embodiment, the compound can have the following formula:
270
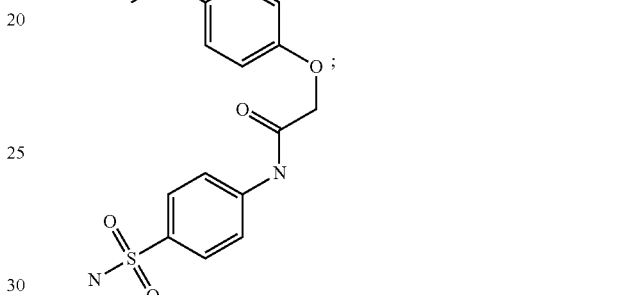
270-330
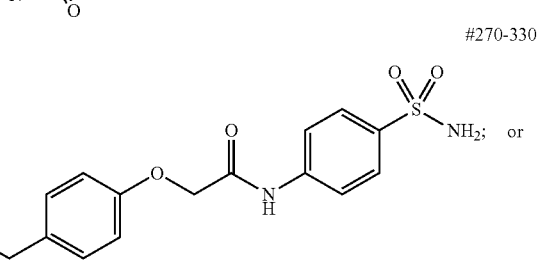
270-331
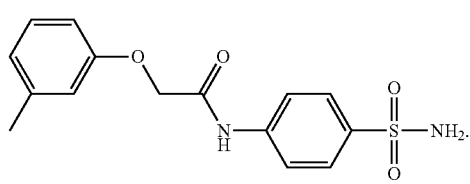
In another embodiment, the compound can have the formula:
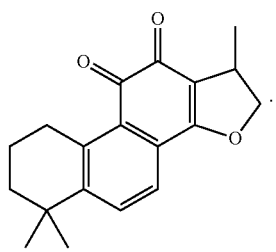 [SMILES: CC1COC2=C1C(=O)C(=O)c1c2ccc2c1CCCC2(C)C]

In yet another embodiment, the compound can have the following formula:

284
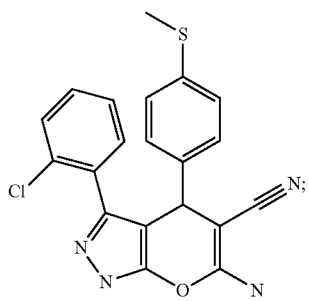

284-332
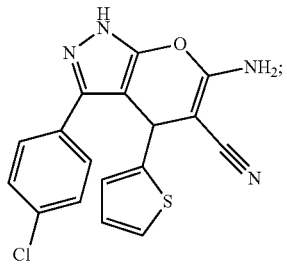

284-335
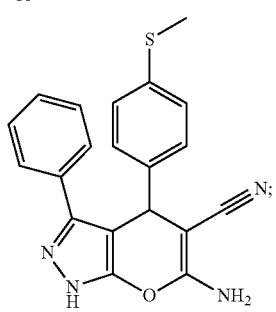

284-336
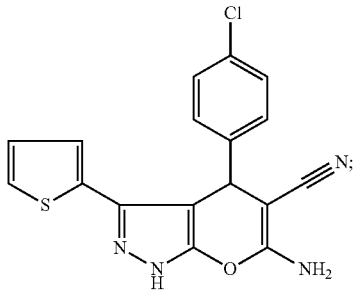

284-446
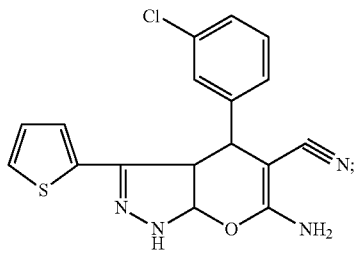

284-447
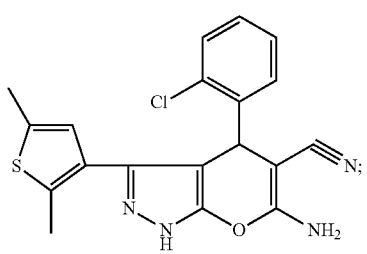

284-460
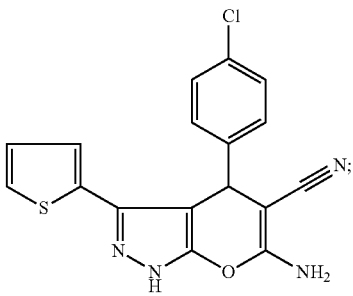

284-463
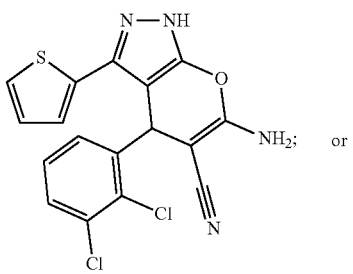

or

284-464
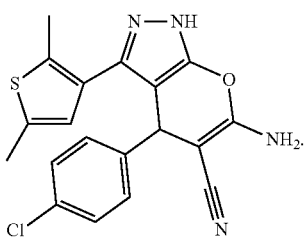

The therapeutic agents or compounds described above can be used for treatment of a disease or condition in a human where selective inhibition of SHP-2, such as human SHP-2 is beneficial. The application therefore provides a method of treating diseases by selectively inhibiting SHP-2 activity. The method includes administering to an animal in need thereof a therapeutically effective amount of a pharmaceutical composition comprising a therapeutic agent or compound in accordance with the application in association with one or more non-toxic, pharmaceutically acceptable carriers and/or diluents and/or adjuvants and if desired other active ingredients.

In some embodiments, it may be beneficial to administer a compound having a greater inhibitory effect on SHP-2 phosphatases as compared to SHP-1phosphatases and other tyrosine phosphatases. Therefore, the therapeutic agent can include a compound having a greater inhibitory effect on SHP-2 phosphatases as compared to SHP-1phosphatases. For example, #324 (see above) has been shown to have high functional specificity for SHP-2 over SHP-1.

The compounds or therapeutic agents described herein can be used to treat conditions and diseases including but not limited to SHP-2 mutation associated diseases. It is known that genetic lesions in SHP-2, a protein tyrosine phosphatase implicated in diverse cell signaling processes, have recently been identified in the inherited developmental disorder Noonan syndrome and a significant portion of various childhood leukemias. In addition, SHP-2 mutations have also been identified in sporadic solid tumors. These mutations cause hyperactivation of SHP-2 catalytic activity. Additionally, the SHP-2 activating mutations appear to play a causal role in the pathogenesis of these diseases. It has also been shown that SHP-2 mutations and Ras or Neurofibromatosis 1 mutations are mutually exclusive in subjects and that single mutations and Ras or Neurofibromatosis 1 mutations are sufficient to induce Noonan syndrome and JMML (Juvenile myelomonocytic leukemia)-like myeloid proliferative disease in mice.

The direct connection between hyperactivation of SHP-2 and pediatric leukemia and Noonan syndrome indicates that SHP-2 can be a useful target for mechanism based therapeutics. Moreover, the therapeutic agents of the invention can be used to treat diseases related to the positive role of SHP-2 in the Ras mutation associated diseases. The Ras pathway is frequently hyperactivated in leukemias and cancers as a result of mutations in the upstream signaling component or Ras itself. Accordingly, the application also contemplates the use of the compounds described herein for the treatment of Noonan syndrome and leukemia (e.g. JMML).

The terms "treatment of Noonan syndrome" and "treatment of leukemia" are intended to include the administration of therapeutic agents of the application to a subject for purposes, which can include prophylaxis, amelioration, prevention or cure of Noonan syndrome or leukemia. Such treatment need not necessarily completely ameliorate Noonan syndrome or leukemia. Further, such treatment can be used in conjunction with other traditional treatments for reducing the inflammatory condition known to those of skill in the art.

The treatment methods can include administering to the subject a therapeutically effective amount of the compounds described herein. Determination of a therapeutically effective amount is within the capability of those skilled in the art. The exact formulation, route of administration, and dosage can be chosen by the individual physician in view of the subject's condition. The term "therapeutically effective amount" refers to an amount (dose) effective in treating a subject, having, for example Noonan syndrome or Leukemia. It is also understood herein that a "therapeutically effective amount" may be interpreted as an amount giving a desired therapeutic effect, whether taken in one dose or in any number of doses, or taken alone or in combination with other therapeutic agents. In the case of the application, a "therapeutically effective amount" may be understood as an amount of the compounds described herein required to treat conditions and diseases, including but not limited to SHP-2 mutation associated diseases, in a subject.

The therapeutic agents described herein can be provided in the form of pharmaceutical compositions. The pharmaceutical compositions of the application can be administered to any animal that can experience the beneficial effects of the compounds of the invention. Foremost among such animals are humans, although the invention is not intended to be so limited.

The pharmaceutical compositions of the application can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route. Particularly preferred is oral administration. The dosage administered will be dependent upon the age, health, and weight of the recipient, kind of concurrent treatment, if any, frequency of treatment, and the nature of the effect desired.

In addition to the pharmacologically active compounds, pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the application are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid-ethylacrylate copolymers, methacrylic acid-ethyl acrylate copolymers, methacrylic acid-methyl methacrylate copolymers and methacrylic acid-methyl methylacrylate copolymers. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples provided are illustrative, but not limiting, of the method and compositions of the application. Other suitable modifications and adaptations of the variety of conditions and parameters normally encountered and obvious to those skilled in the art are within the spirit and scope of the invention.

EXAMPLE 1

CADD in Silico Screening

The 3D structure of SHP-2 in the unphosphorylated state [PDB ID 2 SHP] was retrieved from the Protein DataBank. Following deletion of the SH2 domains, the Reduce algorithm was used to place hydrogen atoms and optimize adjustable groups (OH, SH, NH3+, Met-CH3, and Asn, Gln and His sidechain orientation). To prepare the structure for docking, partial charge and Lennard-Jones parameters from the CHARMM force field including the CMAP were applied. All docking calculations were carried out with DOCK using flexible ligands based on the anchored search method. The solvent accessible surface as calculated with the program DMS using a surface density of 2.76 surface points per Å and a probe radius of 1.4 Å. Sphere sets were calculated with the DOCK associated program SPHGEN. From the full sphere set, sphere clusters in the SHP-2 docking site important for binding pY peptides were identified. On the basis of previous studies, residues involved in intermolecular interactions with residues at the pY+5 position of pY peptides were used to select the docking site. Though no cocrystal structures of SHP-2 exist with PTP-bound pY-peptide, such structural information is available for the close homolog SHP-I. We predicted the likely location of the SHP-2 PTP pY+5 binding pocket based alignment with the SHP-I PTP-PY-peptide cocrystal, and selected spheres in this pocket. Specifically, spheres within 6 Å of residues 255, 258, 261, 498, and 503 were selected, resulting in a set containing 12 spheres and located as shown in FIG. 1. The selected sphere set acted as the basis for initial ligand placement during database searching. The GRID method within DOCK was used to approximate the ligand-receptor interaction energy during ligand placement by the sum of the electrostatic and van der Waals (vdW) components. The GRID box dimensions were 38.5 Å×37.6 Å×38.9 Å centered around the sphere set to ensure that docked molecules were within the grid.

A database of 1.3 million compounds was used for the initial virtual screening. This database of low molecular weight, commercially available compounds had been created in our laboratory by converting files obtained from the vendors in the 2D SDF format to the 3D MOL2 format through a procedure that included geometry generation, addition of hydrogens and charges, and force field optimization using SYBYL6.4 along with in-house programs. The compounds that were screened had between 10 and 40 heavy atoms and less than 10 rotatable bonds. During the docking procedure, each compound was divided into non-overlapping rigid segments connected by rotatable bonds. Segments with more than five heavy atoms were used as anchors, each of which was docked into the binding site in 250 orientations and minimized. The remainder of the molecule was built around the anchor in a stepwise fashion by adding other segments connected through rotatable bonds. At each step, the dihedral of the rotatable bond was sampled in increments of 10° and the lowest energy conformation was selected. During primary docking, each rotatable bond was minimized as it was created without re-minimizing the other bonds. Pruning of the conformational orientations ensured conformational diversity and more favorable energies. Energy scoring was performed with a distant-dependent dielectric, with a dielectric constant of 4, and using an all atom model. Once the whole molecule was built, then it was minimized. The conformation of each molecule with the most favorable interaction energy was selected and saved.

After the primary docking, compounds were chosen for the secondary docking based on their normalized vdW attractive interaction energy scores (see Results and Discussion). Compound selection based on the DOCK energy score favors compounds with higher molecular weight (MW) since their size contributes to the energy score. To minimize this size bias, an efficient procedure was applied in which the DOCK interaction energies (IE) are normalized by the number of heavy atoms N raised to a power ×24.

$$IEnorm = IE/NX$$

Normalization of the vdW attractive energies was done with x=0, 0.33, 0.5, 0.66, and 1 and the MW distributions of the top 50,000 compounds in each category were analyzed to choose the normalized set with a peak closest to MW=300 (see Results and Discussion).

The top 50,000 compounds obtained from the primary database search were screened in a more rigorous and computationally expensive docking procedure, referred to as secondary docking. The procedure described for primary docking was followed with the additional step of minimizing all rotatable bonds simultaneously during the stepwise building of the molecule. Additionally, docking was done to multiple conformations of the PTP domain. In addition to the crystallographic conformation, three additional conformations were used to generate docking grids. These conformations were representative snapshots from the final 4 ns of a 5-ns all-atom explicit-water molecular dynamics trajectory of the PTP domain and were selected by conformational clustering of the heavy atoms in residues 255, 258, 261, 498, and 503 after root-mean squared alignment of the protein Ca atoms to the crystal structure. The resultant snapshots were at the 1.4, 2.4, and 3.8 ns time points, and were representative of the diverse binding site conformations sampled during the molecular dynamics. A new docking sphere set was created for each of these conformations as described above for the crystal structure. Each compound was docked to the crystallographic PTP conformation as well as each of the three molecular dynamics snapshots, and was scored based on the most favorable of the four docking energies. The total interaction energies (electrostatic+vdW) of the 50,000 compounds were normalized, as described above, and the top 1000 compounds from the normalized distribution with a peak closest to MW=300 were selected and subjected to chemical diversity analysis.

Compound Selection Based on Chemical Diversity

Chemical similarity clustering of the top 1000 compounds identified during secondary docking was performed to maximize the chemical diversity of the final compounds selected for biological assay. Clustering calculations were performed using the program MOE (Chemical Computing Group, Inc.). The Jarvis-Patrick algorithm, as implemented in MOE, was used to cluster the compounds using the MACC BITS fingerprinting scheme and Tanimoto coefficient (TC). The algorithm first calculates the MACC BITS fingerprint that encodes the 2D structural features of each compound as a sequence of 0's and 1's. Then, the pairwise similarity matrix between each compound was calculated based on the TC values. TC is a metric that provides a similarity score for two compounds by dividing the fraction of features common to both molecules by the total number of features, where the features are defined by the MACC BITS fingerprints. The similarity matrix is converted into a second matrix in which each TC value is replaced by a 0 or 1 representing similarity values below and above the threshold value (S) provided by the user, respectively. The rows of the new matrix were treated as fingerprints and the 'TC' value between each is calculated. Molecules with values above the selected overlap threshold (T) were put in the same cluster. To generate clusters of reasonable sizes (i.e., 3 to 10 compounds) an iterative procedure was followed in which the T value was gradually decreased by 10 and for each T value three S values (T-10, T-20, T-30) were calculated.

Compounds were chosen from the individual clusters for experimental assay with emphasis on compounds with drug-like physical characteristics as defined by Lipinski et al. Properties considered were the MW, number of hydrogen donors (NHD) and acceptors (NHA) and the log P values as calculated by MOE. However, exceptions were made when all compounds in a cluster had one or more physical characteristics beyond the range defined by Lipinski et al. The resultant chemically diverse list of approximately 200 compounds selected via CADD were purchased from ChemDiv (San Diego, Calif.), ChemBridge (San Diego, Calif.), or Specs (Wakefield, R.I.) and dissolved in dimethyl sulfoxide (DMSO) at a stock concentration of 25, 50, or 100 mM. The purity of the active compounds was verified by mass spectrometry.

In vitro and In vivo Phosphatase Assay

Candidate compounds were screened using the in vitro protein tyrosine phosphatase (PTP) assay kit (Sigma, St. Lois, Mo.). SHP-2 PTP domain GST fusion protein purified in house was used as the enzyme and a phospho-peptide corresponding to the surrounding sequence of $pTyr^{1146}$ in the insulin receptor (Thr-Arg-Asp-Ile-Tyr[$PO_3H_2$]-Glu-Thr-Asp-Tyr-Tyr) were used as the substrate. The assay determines free phosphate generated by dephosphorylation of the PTP substrate using the Malachite Green reagent. Briefly, 0.5 µg of GST-SHP-2 PTP was incubated in 40 µL assay buffer (25 mM Tris-HCl, PH7.4, 50 mM NaCl, 5 mM DTT, and 2.5 mM EDTA) with test compounds at various concentrations or DMSO at room temperature for 30 min. The PTP substrate was then added to a final concentration of 0.2 mM. The system was incubated at 30° C. for 30 min. Finally, 50 µl of Malachite Green solution was added and $OD_{620}$ was measured after 5 min. In the phosphatase assays for SHP-1, CD45, TC-PTP, PTP-MEG2 (PTPN9), and LAR (PTPRF), procedures were similar, with the exception that GST-SHP-1, GST-CD45 cytoplasmic domain, GST-TC-PTP, GST-PTP-MEG2 PTP domain, and GST-LAR PTP domain purchased from Biomol International, L.P. (Plymouth Meeting, Pa.) were used instead as the enzymes.

For the in vivo phosphatase assay, mouse embryonic fibroblasts were used to assess the activities of the test compounds in inhibiting epidermal growth factor (EGF)-induced activation of SHP-2 catalytic activity. WT and mutant fibroblasts derived from activating mutation of SHP-2 D61G knock-in mice (SHP-2D61G/D61G)10 were starved in serum-free medium overnight and the tested compounds (100 µM) were added in the last 1 hour. Cells were then stimulated with EGF (50 ng/mL) for 10 min. The cells were harvested and lysed in RIPA buffer (50 mM Tris-HCl pH 7.4, 1% NP-40, 0.25% Na-deoxycholate, 150 mM NaCl, 1 mM EDTA, 1 mM NaF, 10 µg/mL leupeptin, 10 µg/mL aprotin, and 1 mM PMSF). Whole cell lysates (500 µg) were immunoprecipitated with 1 µg of anti-SHP-2 antibody. Immunoprecipitates were washed three times with HNTG buffer (20 mM Hepes pH 7.5, 150 mM NaCl, 1% Glycerol, and 0.1% Triton X-100) and assayed for the catalytic activity using the phosphatase assay as described above.

Ba/F3 Cell Proliferation Assay

To test the effects of the active compounds on IL-3-induced cellular response, Ba/F3, an IL-3 dependent murine pro-B lymphoma cell line, was used for the assay. Ba/F3 cells were seeded into 96-well plates ($2 \times 10^4$ cells/well) in the RPMI-1640 medium supplemented with 10% fetal bovine serum (FBS), recombinant mouse IL-3 (1 ng/mL), and test compounds (100 and 200 µl). Three days later, cell number was determined using the MTS cell proliferation kit (Promega Life Science, Madison, Wis.).

Cell Proliferation Assay

To test the effects of the active compounds on SHP-2-mediated cellular proliferation, Ba/F3, an IL-3 dependent hematopoietic cell line, mouse embryonic fibroblasts (MEFs), and H661 lung cancer cell line with SHP-2 activating mutation N58S were used for the assays. Cells were seeded into 96-well plates ($2 \times 10^4$ cells/well) in the RPMI-1640 (for Ba/F3 cells) or DMEM (for MEFs and H661 cells) medium supplemented with 10% fetal bovine serum (FBS) and test compounds at various concentrations. For the Ba/F3 cell assay, recombinant mouse IL-3 (1 ng/mL) was included in the culture medium. Two days later, cell number was determined using the MTS cell proliferation kit (Promega Life Science, Madison, Wis.).

Hematopoietic Progenitor Cell Colony Formation Assay

To determine cellular response of myeloid progenitors to IL-3, bone marrow cells ($5 \times 10^4$ cells/ml) freshly harvested from C57BL6 mice were assayed for colony forming units (CFUs) in 0.9% methylcellulose IMDM medium containing 30% FBS, glutamine ($10^{-4}$ M), β-mercaptoethanol ($3.3 \times 10^{-5}$ M), and IL-3 (10 ng/ml). After 7 days of culture at 37° C. in a humidified 5% $CO_2$ incubator, hematopoietic cell colonies (primarily CFU-GM) were counted under an inverted microscope.

Fluorescence Titrations

For all experiments, Purified SHP-2 PTP domain GST-fusion protein was diluted into 20 mM Tris-HCl, pH 7.5. Fluorescence spectra were recorded with a Luminescence Spectrometer LS50 (Perkin-Elmer, Boston, Mass.). Titrations were performed by increasing the test compound concentration while maintaining the SHP-2 protein concentration at 3 µM. Contributions from background fluorescence of the inhibitors were accounted for by subtracting the fluorescence of the inhibitors alone from the of the protein-inhibitor solution. The excitation wavelength was 295 nm and fluorescence was monitored from 360 to 500 nm. All reported fluorescence intensities are relative values and are not corrected for wavelength variations in detector response.

Selection of the Docking Site in the SHP-2 Catalytic Domain

SHP-2 has over 60% sequence identity with the homologous SHP-1 phosphatase, although the latter protein plays an opposing role to SHP-2 in hematopoietic cell signaling. In order to identify SHP-2 PTP specific inhibitors, a structural alignment between SHP-2 and SHP-1 was performed in order to search for a potential drug-docking pocket in the SHP-2 catalytic domain that would be specific for that protein. Such a site must be structurally different than that present in SHP-1 allowing for specific interactions to occur between the compounds and SHP-2 that could not occur between the compounds and SHP-1 or other phosphatases. Not surprisingly, the residues that perform the pY hydrolysis in both SHP-2 and SHP-1, i.e., the catalytic site, are identical both in sequence and in spatial location. Thus, any SHP-2 inhibitor that binds to the catalytic site would be expected to have cross-reactivity with SHP-1, as well as with other PTP-domain containing proteins that also utilize this spatial arrangement of amino acids for catalysis.

Using the program SPHGEN, potential binding sites on the SHP-2 protein were identified and the sites in the SHP-2 PTP domain were analyzed in detail. This led to the identification of a putative pocket in the surface of the protein that appeared to be different from that in SHP-1 in both structure and amino acid composition. As demonstrated by a co-crystal structure, in the case of SHP-1 this pocket binds the acidic C-terminal aspartic acid at the pY+4 position of a pY peptide. In contrast, SHP-2 PTP has been shown in assays to preferentially bind to pY peptides with a basic residue at the pY+5 position, and our protein alignment suggests that the chosen binding pocket is a logical place for this specific interaction to be occurring. FIG. 1 illustrates the pY-peptide binding clefts of the two proteins and the particular pocket in the SHP-2 cleft used as the target binding site for the CADD screening.

Primary Database Screening

Compound selection from the primary database screen was based on the vdW attractive energy, as previously performed. Use of this term selected compounds that have favorable steric interactions with the protein and avoids the selection of compounds whose interaction with the protein are dominated by one or two electrostatic interactions. Use of the vdW attractive term for scoring does not exclude the selection of compounds for which favorable electrostatic interactions with the protein occur as the total energy (i.e. electrostatic and vdW terms) was used for the actual docking process (i.e. posing). Use of the vdW attractive energy without any normalization yielded a MW distribution for the top scoring 50,000 compounds with a peak at 410 Da (FIG. 2A). Based on this histogram, approximately 10% of those compounds were above a MW of 500 Da. As drug-like compounds typically have MWs below 500 Da and lead compounds, the target of the present study, have even lower MWs, the goal was to choose a distribution with a peak at 300 Da via the previously developed MW normalization procedure. Using N, N0.66, N0.5, and N0.33 normalization the peaks of the histograms of the top scoring 50,000 compounds were at MW values of 230, 230, 290, and 350 Da, respectively; thus, N0.5 normalization was chosen. The MW probability distribution of the entire database screened in the present study is centered at 360 Da, as is the average of the World Index Database. The resultant low MW of the lead compounds identified by normalized scoring allows the addition of functional groups during future lead optimization efforts.

It should be noted that significant overlap of compounds occurred for the different normalization schemes. Of the 50,000 compounds selected via N0.5 normalization, 85% compounds were common in the N0.33 set, 87% in the N0.66 set, 67% in the N set, and 58% in the set of non normalized (i.e., N0) compounds. Thus, it may be assumed that compounds with highly favorable interaction orientations with the protein binding site were not being excluded by the normalization procedure.

Secondary Database Screening

Secondary screening of the 50,000 compounds selected from the primary screen involved a more exhaustive and computationally demanding conformational search of the docked molecules. As compounds with good steric fit were selected from the primary screen, electrostatic as well as vdW interaction energies were used for the selection of compounds from the secondary screen. Additionally, each compound was docked not only to the crystal PTP conformation, but also to three other conformations from molecular dynamics simulation, and the most favorable interaction energy was taken as that compounds score. The inclusion of additional conformations helps to account for the conformational heterogeneity of protein surfaces in a solvated environment, and aims to address a potential limitation of representing the protein as a rigid body during grid-based docking. The total interaction energies were normalized using different powers of N and the MW distributions of the top 1000 compounds was determined for each normalization scheme (FIG. 2B). For the top 1000 compounds selected via the N, N0.66, N0.5, and N0.33 normalization, the distribution peaks were at 190, 210, 250, and 330 Da, respectively (FIG. 2B). The peak for the top 1000 compounds without normalizing the energies was 410 Da (FIG. 2B). The top 1000 scoring compounds in the set obtained after N0.33 normalization was chosen to select compounds in the target MW range discussed above while avoiding molecules, which were too small and lacking adequate structural diversity for lead or drug-like candidates.

Final Compound Selection

The final list of compounds to be submitted for experimental testing should be chemically diverse to increase the probability of identifying unique leads. To facilitate selection of diverse compounds, a clustering algorithm that distributes the compounds into groups (clusters) of structurally similar compounds with compounds across clusters being dissimilar was applied. One or more compounds are then selected from each cluster for experimental validation. The selection process for choosing a compound from a particular cluster was based on Lipinski's Rule of 5: MW of less than 500 Da and the number of hydrogen bond donors, the number of hydrogen bond acceptors and log P values each less than 5, although exceptions were made for clusters that did not contain members fulfilling these criteria. Compounds fulfilling these empirical rules have an increased likelihood of demonstrating good ADME properties, which is an important consideration when the ultimate goal is to develop a therapeutic. A total of 236 compounds were thus selected from the list of 1000, 165 of which were subsequently obtained from commercial sources and subjected to biological assays.

In vitro Experimental Assay of the Candidate Compounds Identified by CADD

Figure 3A:
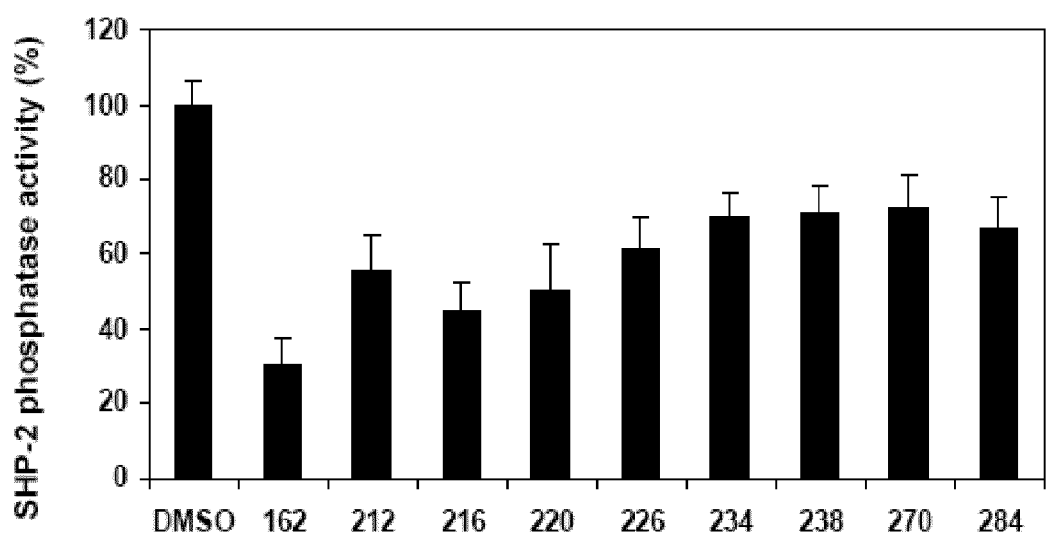
FIG. 3 illustrates inhibitory effects of the nine active compounds on the phosphatase activity of SHP-2. (A) Candidate compounds identified by CADD were screened using the in vitro tyrosine phosphatase assay as described in the Experimental Section. Compounds were dissolved in DMSO at 100 μM. Shown are results of the 9 active compounds. (B) Chemical structures of the 9 active compounds. (C) The inhibitory effect of compound #162 on SHP-2 activity was tested at the indicated concentrations using the in vitro phosphatase assay.
Figure 3C:
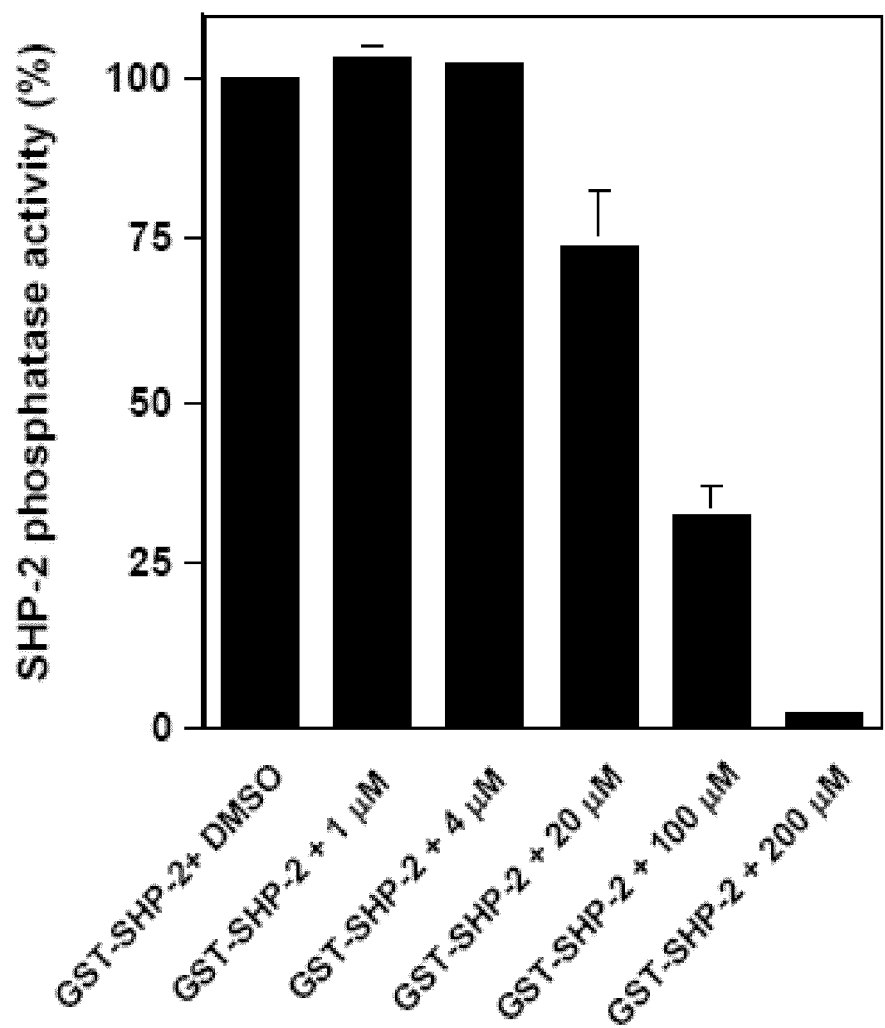

Candidate compounds identified by CADD were screened by the in vitro tyrosine phosphatase assay as described in the Experimental Section. The GST-SHP-2 PTP domain fusion protein was incubated with the compounds at room temperature for 30 min before the phospho-peptide substrate was added to the assay systems, allowing compounds to bind to target sites in SHP-2. Each test compound was dissolved in DMSO. Initial concentration of the test compounds was 100 µM. In the experimental assay, DMSO was included as the negative control and sodium orthovanadate (100 µM), a general non-specific tyrosine phosphatase inhibitor, was used as the positive control. From the 165 commercially available compounds tested, we identified 9 compounds that inhibit SHP-2 catalytic activity with various efficiencies (FIG. 3A). The structures of the 9 active compounds are shown in FIG. 3B. Except #238, which does not seem to be bioavailable, other 8 compounds are drug-like. At a concentration of 100 µM, the five most active compounds (#162, #216, #220, 212, and #226) inhibited 70%, 55%, 50%, 45%, and 40% of SHP-2 enzymatic activity, respectively. The inhibitory effects of the compounds were dose-dependent. For example, at 200 µM, #162 essentially blocked the catalytic activity of SHP-2 (FIG. 3C).

Figure 4A:
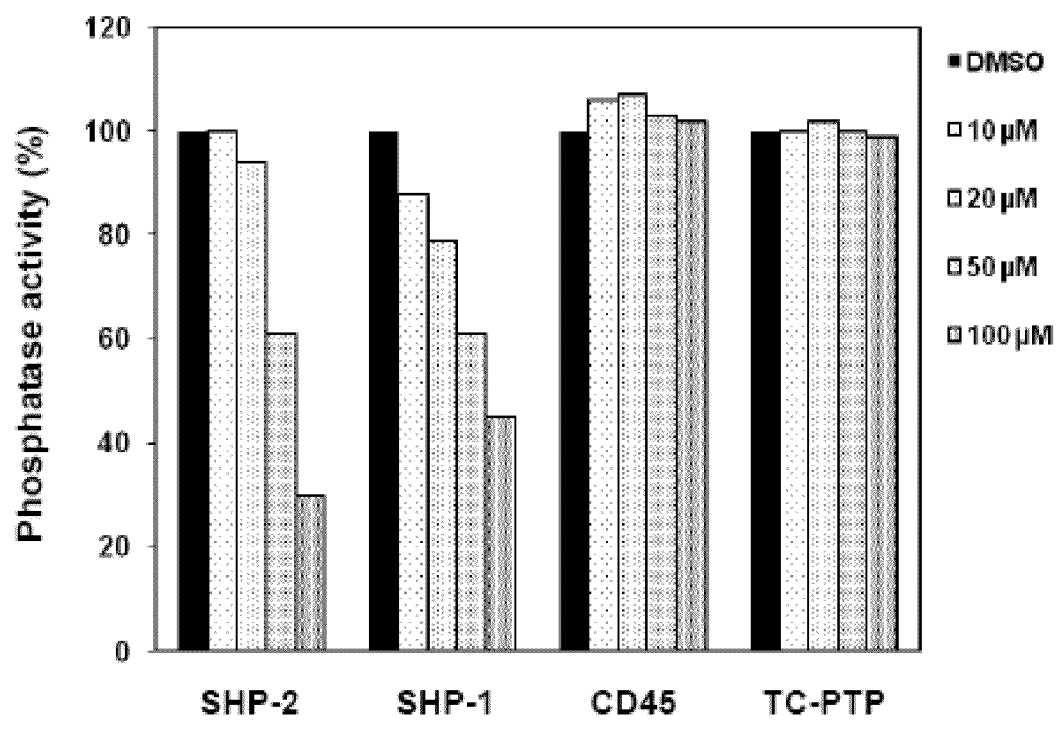
FIG. 4 illustrates functional specificity of the top three active compounds. Compounds #162 (A), #216 (B), and #220 (C) at the indicated concentrations were subjected to the phosphatase assays using SHP-2, SHP-1, CD45, and TC-PTP as enzymes. DMSO was used as negative controls.
Figure 4B:
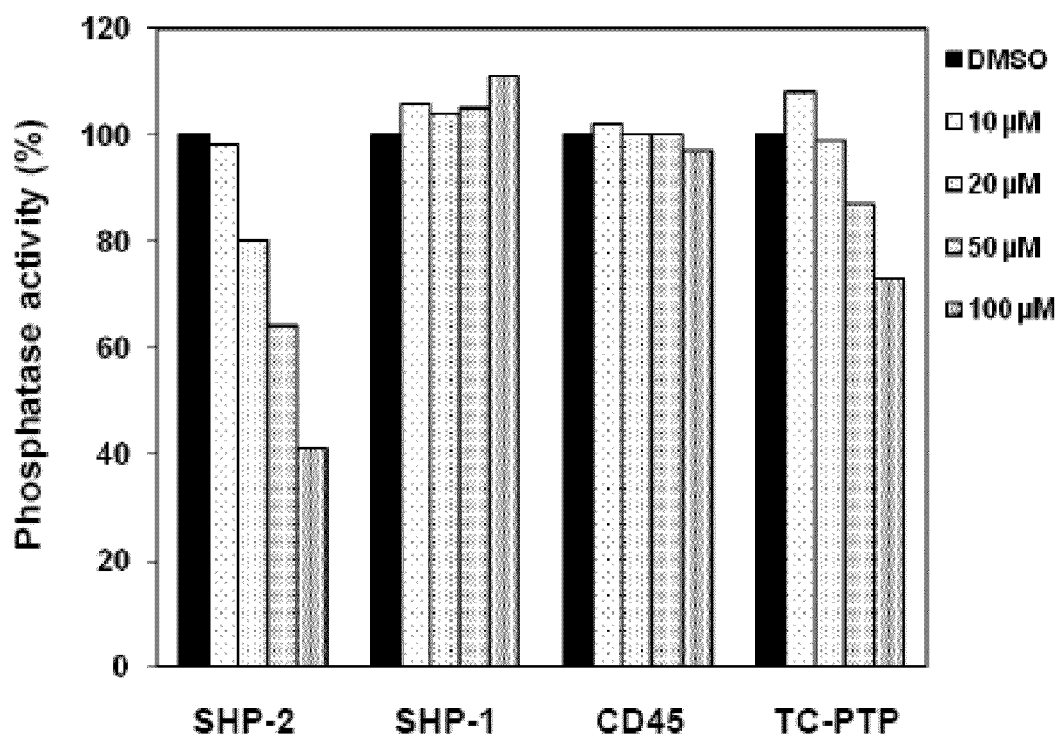
Figure 4C:
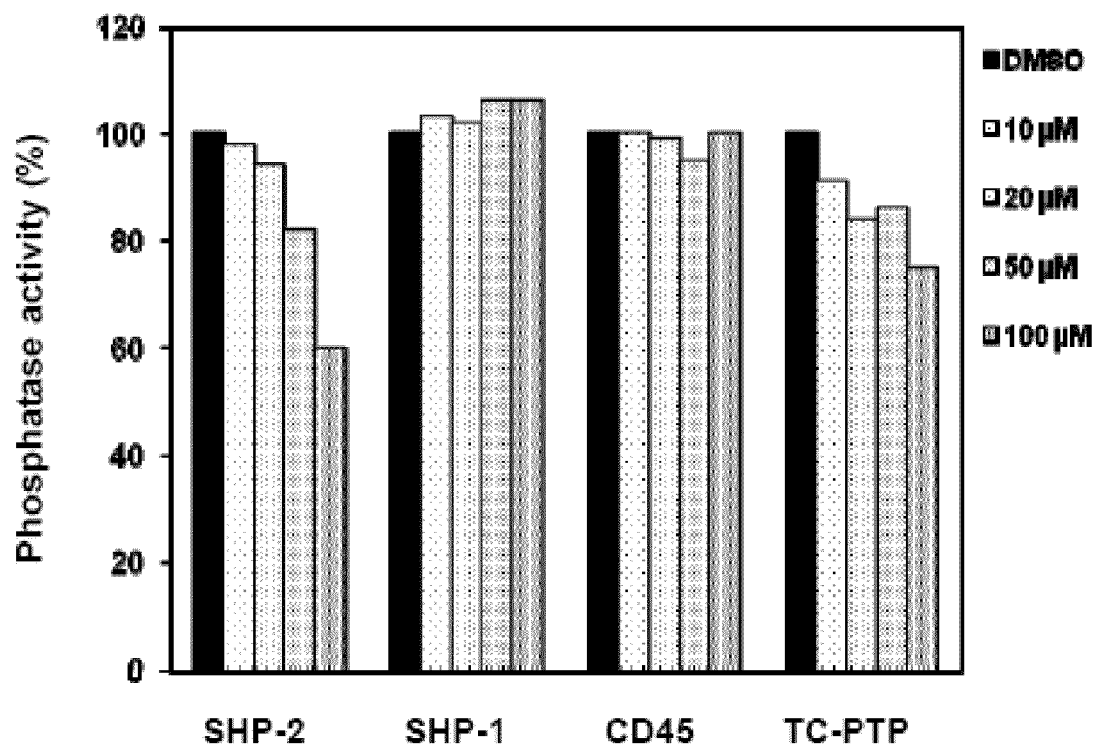

We next determined functional specificities of the three most active compounds, i.e., the activities on related tyrosine phosphatases, in particular those phosphatases that are highly expressed in hematopoietic cells, such as SHP-1, CD45, and TC-PTP. As shown in FIG. 4A, compound #162 equally inhibited SHP-2 and SHP-1 phosphatases, but it did not inhibit the other two phosphatases tested. Compounds #216 and #220 selectively inhibited SHP-2 vs. SHP-1. Both of them also showed slight inhibition of TC-PTP (FIGS. 4B and 4C). It is worth mentioning that although compound #162 did not show selectivity between SHP-2 and SHP-1, this compound is still useful for future studies of SHP-2 function in non-hematopoietic cells, since expression of SHP-1 phosphatase is restricted to hematopoietic and epithelial cells.

In vivo Effects of the Active Compounds on SHP-2-Mediated Cellular Function

Figure 5A:
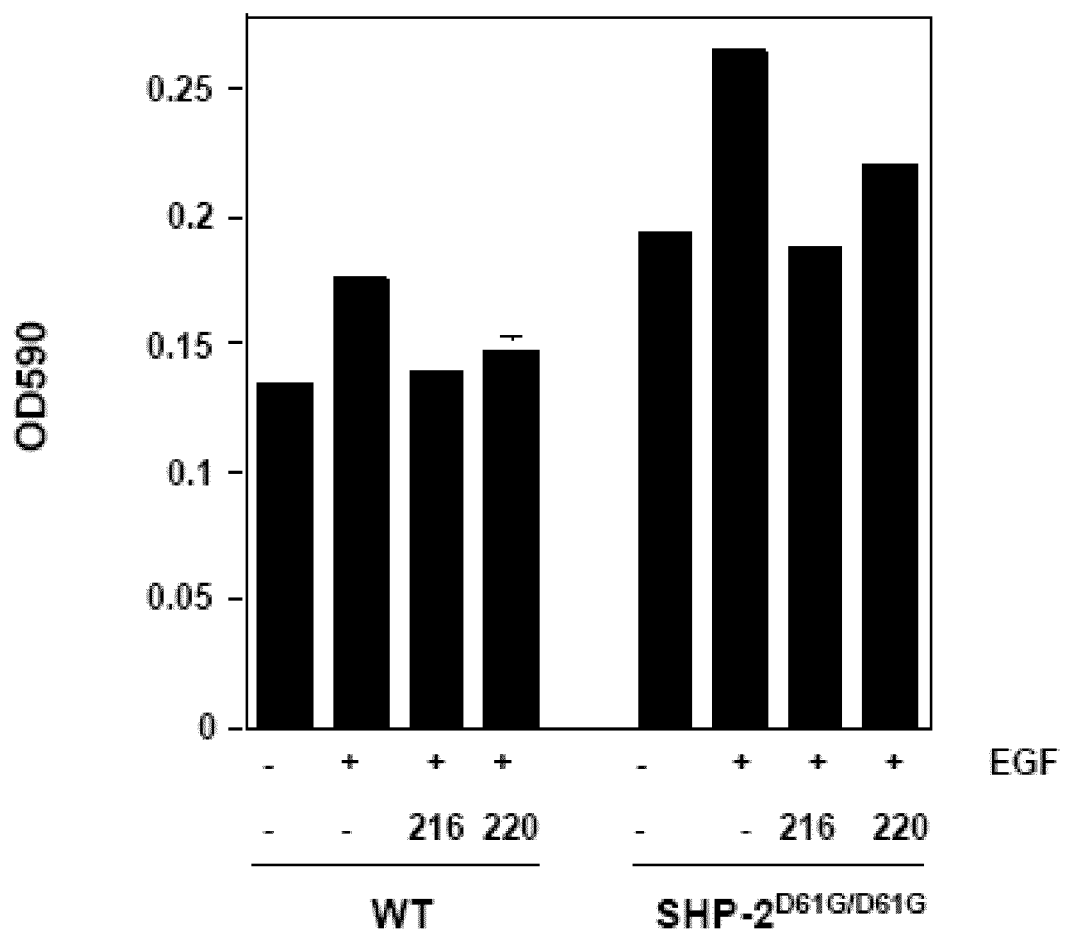
FIG. 5 illustrates in vivo effects of active compounds on SHP-2 activity and SHP-2-mediated signaling. (A) WT and mutant embryonic fibroblasts derived from activating mutation SHP-2 D61G knock-in mice were starved in serum-free medium overnight and were treated with the indicated compounds in the last 1 hour. Cells were then stimulated with EGF (20 ng/mL) for 10 min. Whole cell lysates were prepared and immunoprecipitated with anti-SHP-2 antibody. Immunoprecipitates were washed and then subjected to the in vitro phosphatase assay as described in the text. (B) Ba/F3 cells were deprived of IL-3 for 8 hours. The cells were treated with the indicated compounds 1 hour prior to the stimulation with IL-3 (2 ng/mL). Cells were harvested after the indicated periods of time. Whole cell lysates were prepared and examined for Erk activation with anti-phospho-Erk immunoblotting. The blot was striped and reprobed with anti-pan Erk antibody to examine protein loading.
Figure 5B:
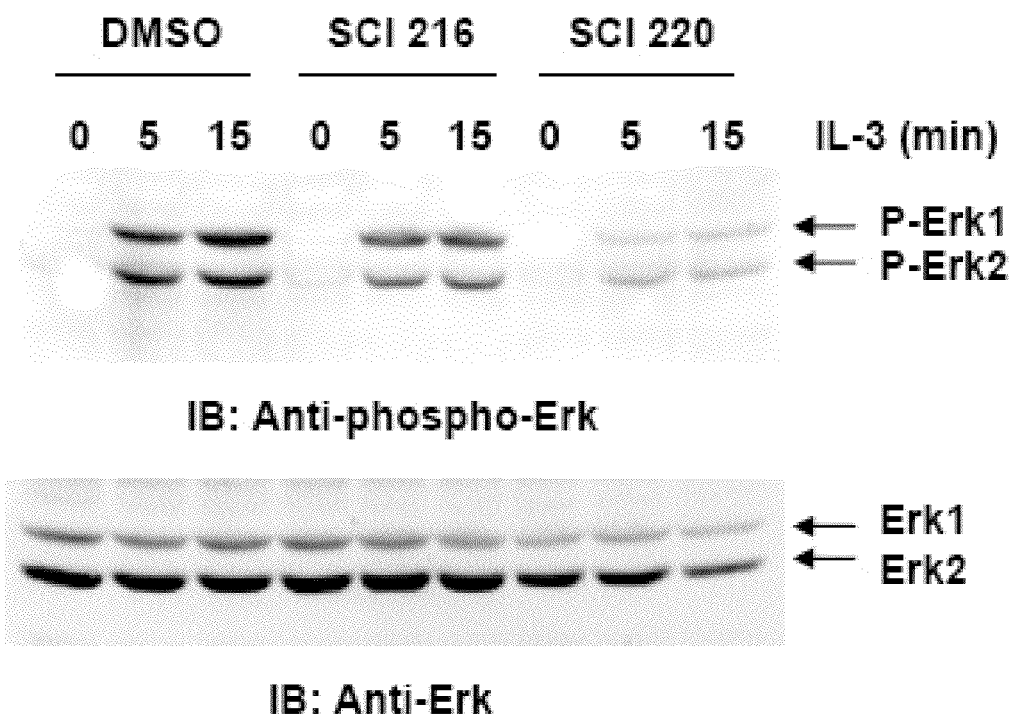

We next tested whether the active compounds are effective in cells. Compounds #216 and #220 that selectively inhibit SHP-2 but not SHP-1 were used to treat WT and mutant mouse embryonic fibroblasts with an activating mutation D61G in SHP-2. Activation of SHP-2 in response to EGF stimulation was determined using the immunocomplex phosphatase assay. Compared to WT SHP-2, catalytic activity of SHP-2 D61G mutant in the mutant cells was increased both at the basal level and following EGF stimulation (FIG. 5A), consistent with previous studies. In the presence of the inhibitors, EGF-induced activation of SHP-2 was blocked in both WT and SHP-2D61G/D61G cells (FIG. 5A). We also examined IL-3-induced activation of Erk kinases in hematopoietic cells that requires SHP-2 catalytic activity. Preincubation of Ba/F3 cells with the inhibitors suppressed Erk activation by IL-3 (FIG. 5B), in agreement with previous results that SHP-2 catalytic activity is required for optimal activation of Erk kinases. These data suggest that the two inhibitors tested are effective in inhibiting SHP-2 in cells.

Figure 6:
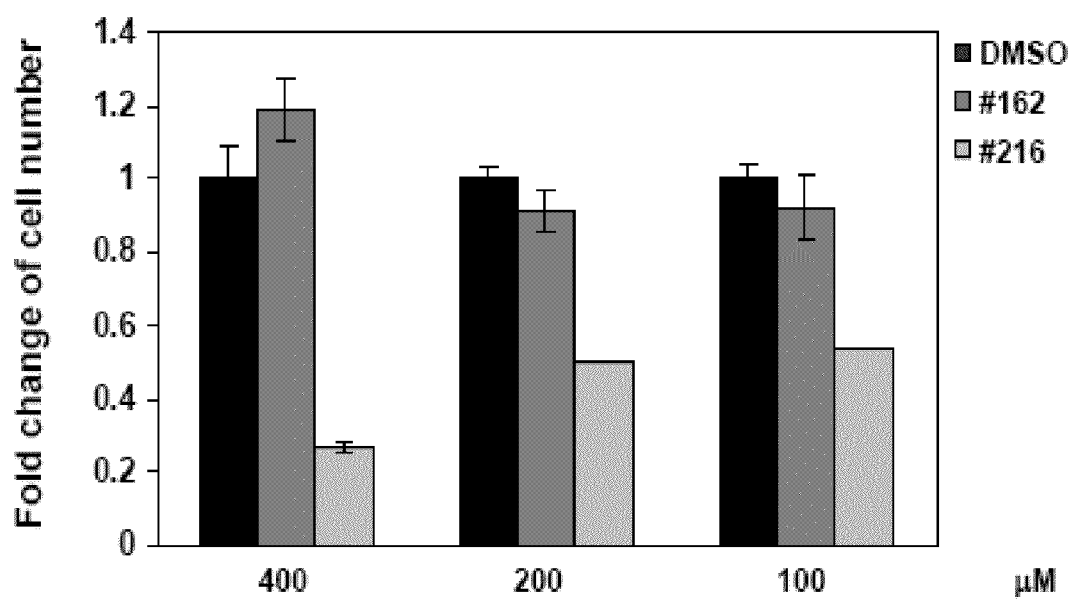
FIG. 6 illustrates the effects of SHP-2 inhibitors on cell proliferation. Ba/F3 cells were cultured in IL-3(1 ng/mL) containing medium supplemented with compounds #162 and #216 (100 or 200 μM). DMSO was included at negative controls. Cell numbers were determined 72 hours later using the MTS assay.

To further determine the effects of the active compounds on cellular function mediated by SHP-2, we treated Ba/F3 cells with #162 and #216 (#220 showed modest acute cytotoxicity, and was therefore excluded from the test) and assessed cell proliferation response to IL-3. As shown in FIG. 6, treatment of Ba/F3 cells with #162 did not significantly disturb cell growth, possibly because #162 does not have selectivity in between SHP-2 and SHP-1 phosphatases. However, treatment with #216 greatly decreased IL-3-stimulated cell growth, consistent with the overall positive role of SHP-2 catalytic activity in cellular response to IL-3.

Figure 7:
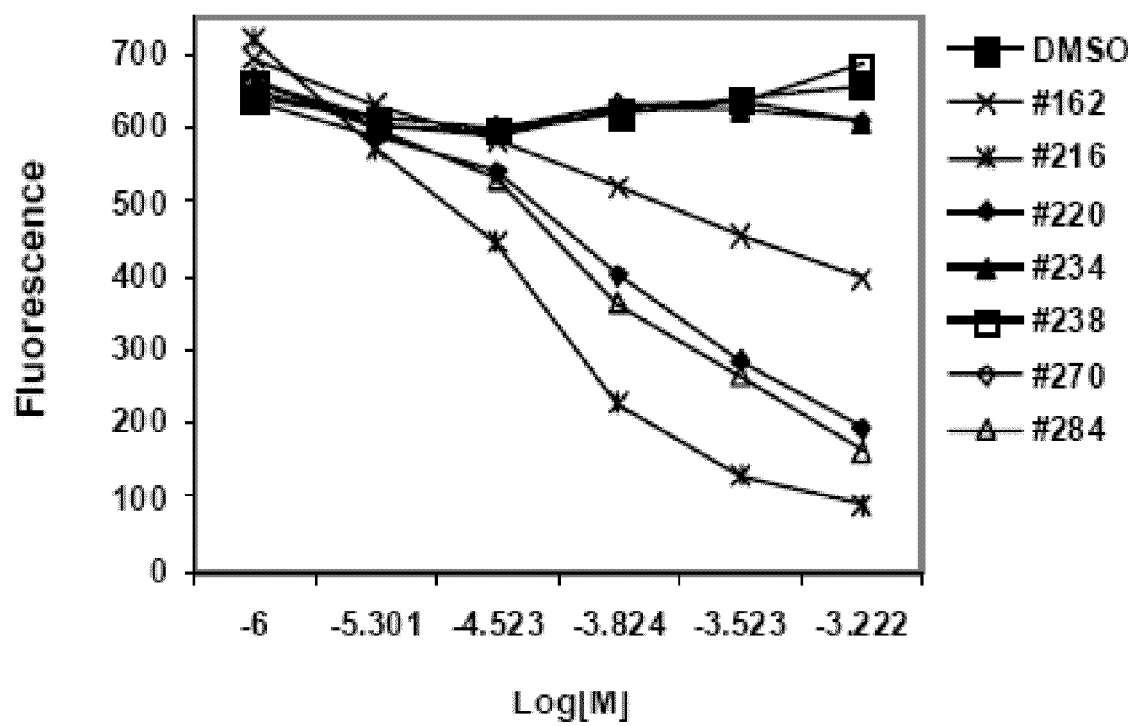
FIG. 7 illustrates the effects of active compounds on SHP-2 fluorescence. Fluorescence titration of SHP-2 was done as described in the Experimental Section. The fluorescence is plotted against the log concentration in moles/liter (Log [M]) for each compound.

Verification of the Binding Between Active Compounds and SHP-2 via Fluorescence Titrations To validate that the active compounds identified were binding directly to the SHP-2 protein, we determined whether the active compounds directly interacted with the SHP-2 PTP domain using fluorescence quenching and taking advantage of the four tryptophans in the PTP domain, with Trp248 located 15 Å from the putative pY+5 pocket and Trp423 located 8 Å from the phosphatase active site. Of the 9 active compounds identified by the in vitro phosphatase assay, #216, #284, and #220 showed strong quenching of SHP-2 fluorescence, while quenching occurred to a small extent at the higher concentrations with #162. The other three compounds (#234, #238, and #270) did not show significant quenching (FIG. 7). Compounds #212 and #226 showed strong fluorescence at the excitation wavelength of 295 mm. Therefore, their binding to SHP-2 protein could not be determined using this measurement. Thus, the fluorescence quenching experiments indicate that at least four active compounds identified do directly bind to SHP-2, thereby leading to their biological activities.

Predicted Binding Mode Between Active Compounds and the SHP-2 PTP Domain

Figure 8:
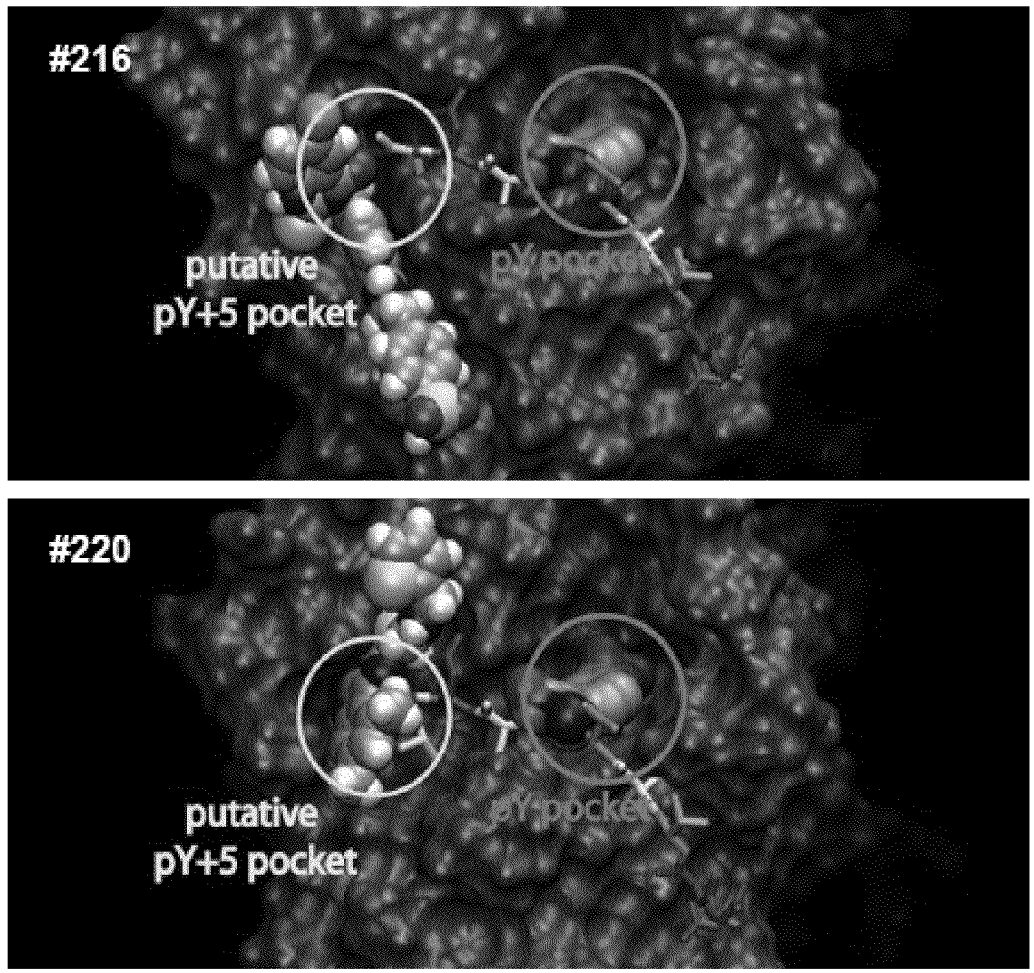
FIG. 8 illustrates predicted binding modes of compounds #216 and #220. Top: #216 bound to the 2.4-ns molecular dynamics conformation of SHP-2 PTP. Bottom: #220 bound to the crystallographic conformation [PDB ID 2SHP] of SHP-2 PTP. The crystallographic conformation of a SHP-1 bound pY-peptide [1FPR] after alignment of the SHP PTP domains illustrates that both inhibitors bind to the putative pY+5 pocket of SHP-2 PTP and not to the pY-binding pocket (the pY-peptide pY residue is shown as a molecular surface and other residues as lines colored by residue type: red=acidic, green=polar, white=hydrophobic).
Figure 9:
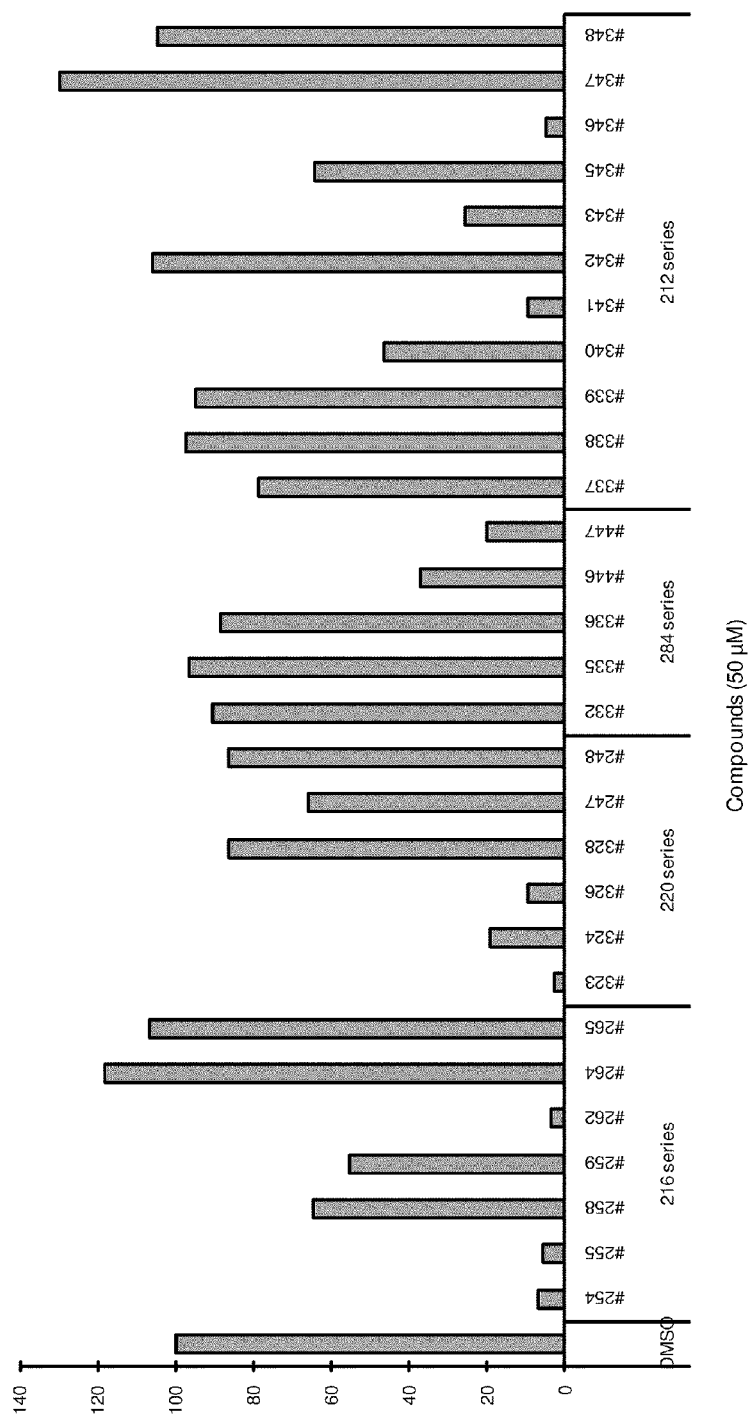
FIG. 9 illustrates in vitro experimental screening of candidate compounds collected from in silico similarity search. Candidate compounds identified by in silico similarity search based on the 9 active compounds initially discovered were screened using the in vitro tyrosine phosphatase assay as described in Experimental Procedures. Compounds were dissolved in DMSO at 50 μM.

The placement of the sphere sets for docking in the putative pY+5 pocket of the SHP-2 PTP pY-peptide binding group constrains the docking procedure to place compounds in this region of the protein. The SHP-2 vs. SHP-1 specificity exhibited by compounds #216 and #220 suggest that this strategy helped in discovering compounds that targeted this pocket. Analysis of the docked poses of these two compounds from the secondary docking shows that both bind this pocket and neither bind to the pY pocket (i.e. catalytic site), which is essentially identical in SHP-1 and SHP-2 (FIG. 8). Also, while #220 bound most favorably to the crystallographic conformation of SHP-2 PTP, #216 bound most favorably to the molecular dynamics snapshot taken at 2.4 ns. These two PTP conformations exhibit different surfaces adjacent to the putative pY+5 pocket, and the two compounds bind in contrasting poses accordingly. In the case of #220, a second shallower pocket immediately adjacent to the pY+5 pocket serves to accommodate the portion of the compound that is not in the pY+5 pocket (FIG. 8, bottom). In contrast, the region of #216 not in the pY+5 pocket extends in the opposite direction on the surface of the protein. It binds to a groove that is created by normal thermal fluctuations in the PTP residues during the course of the molecular dynamics simulation (FIG. 8. top). This groove is not well-defined in the crystallographic conformation, hence the preferential binding of #216 to the molecular dynamics conformation vs. the crystallographic conformation. Although the inclusion of additional non-crystallographic conformations generated by explicit-water molecular dynamics and used for the secondary docking significantly increases the computational cost of the CADD procedure, in the case of SHP-2 PTP it has led to the discovery of one of the more promising lead compounds.

In vivo Effects of the Compound #324 on SHP-2-Mediated Cellular Function

FIG. 11 illustrates inhibition of Ba/F3 cell proliferation by active compounds. Ba/F3 cells were cultured in IL-3 (1 ng/mL) containing medium supplemented with active compounds at the indicated concentrations. DMSO was included at negative controls. Cell numbers were determined 48 hours later using the MTS assay. Shown are the results of a representative compound #324. Note: Both SHP-2 and SHP-1 phophatases are expressed in Ba/F3 cells that depend on IL-3 for growth. While SHP-1 plays a negative role in IL-3 induced cellular responses, SHP-2 plays an overall positive role in cellular response to IL-3. The data that Ba/F3 cell growth in IL-3 containing medium is suppressed by the active compounds we identified suggest that these compounds preferentially inhibit SHP-2 phosphatase.

FIG. 12 illustrates fibroblasts with SHP-2 activating mutation E76K are more sensitive to active compounds than wildtype fibroblasts. Mouse embryonic fibroblasts, wildtype and SHP-2 E76K mutant, were cultured in DMEM medium supplemented with active compounds at the indicated concentrations. DMSO was included at negative controls. Cell numbers were determined 48 hours later using the MTS assay. Shown are the results of a representative compound #324. Note: The E76K mutation is the most frequent and the most potent activating mutation of SHP-2 identified in human leukemias and solid tumors.

FIG. 13 illustrates A). Myeloid progenitors with SHP-2 activating mutation E76K are more sensitive to active compounds than wildtype progenitor cells. Bone marrow cells were harvested from wildtype and mutant mice with SHP-2 E76K mutation. IL-3 induced myeloid progenitor cell colony (CFU-GM) formation assays were performed as described in the Examples in the presence of various concentrations of active compounds. Shown are the results of a representative compound #324. B). Inhibition of growth factor-independent colony formation of myeloid progenitors with SHP-2 activating mutation E76K by active compounds. Bone marrow cells were harvested from wildtype and mutant mice with SHP-2 E76K mutation. The cells were assayed for CFU-GM without cytokines in the presence of various concentrations of active compounds. Shown are the results of a representative compound #324.

FIG. 14 illustrates A). H661 lung cancer cells with SHP-2 activating mutation N58S are more sensitive to active compounds than H596 lung cancer cells without SHP-2 mutation. H661 and H596 cells were cultured in DMEM medium supplemented with active compounds at the indicated concentrations. DMSO was included at negative controls. Cell numbers were determined 48 hours later using the MTS assay. Shown are the results of a representative compound #324. B). H661 lung cancer cells with SHP-2 activating mutation N58S are more sensitive to active compounds than H596 lung cancer cells without SHP-2 mutation. H661 and H596 cells were cultured in DMEM medium supplemented with active compounds (10 µM) for the indicated periods of time. DMSO was included at negative controls. Cell numbers were determined using the MTS assay. Shown are the results of a representative compound #324.

Figure 15:
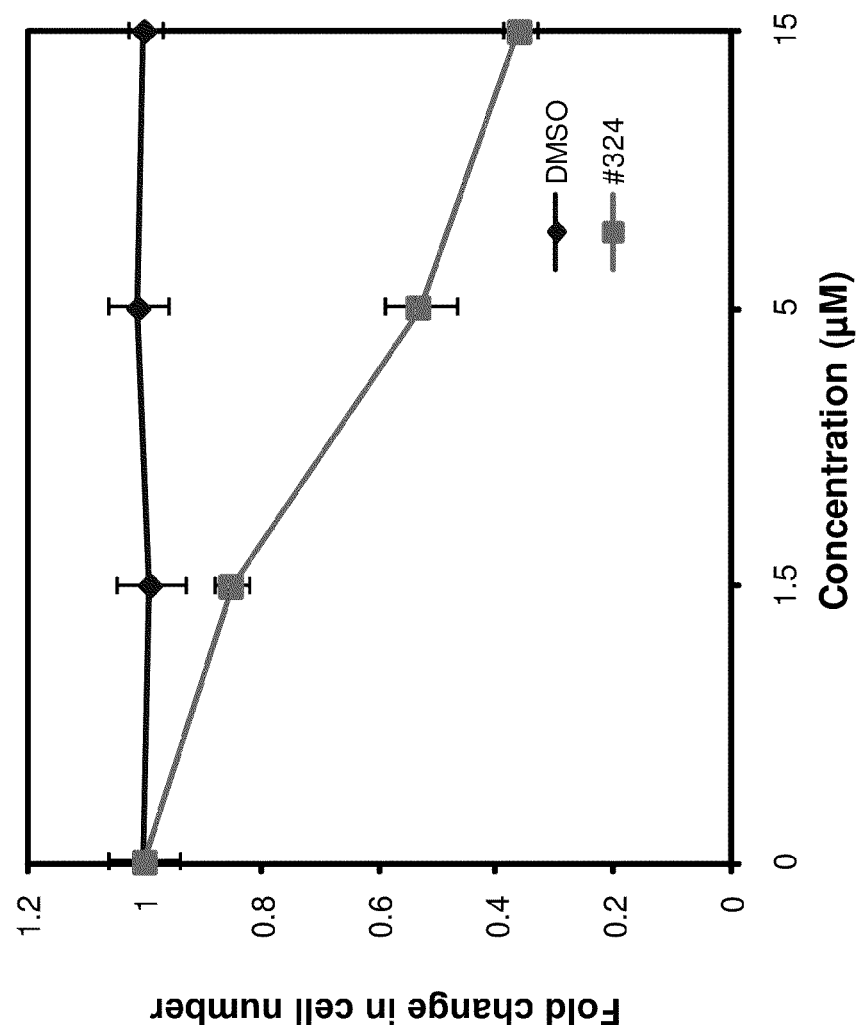
FIG. 15 illustrates inhibition of growth factor-independent colony formation of myeloid progenitors with SHP-2 activating mutation E76K by active compounds. JMML patient bone marrow cells were harvested from mutant mice with SHP-2 E76K mutation and were cultured in DMEM medium supplemented GM-CSF. DMSO was included at negative controls. Cell numbers were determined using the MTS assay. Shown are the results of a representative compound #324.

FIG. 15 illustrates inhibition of growth factor-independent colony formation of myeloid progenitors with SHP-2 activating mutation E76K by active compounds. JMML patient bone marrow cells were harvested from mutant mice with SHP-2 E76K mutation and were cultured in DMEM medium supplemented GM-CSF. DMSO was included at negative controls. Cell numbers were determined using the MTS assay. Shown are the results of a representative compound #324.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating leukemia in a subject comprising, administering to the subject a therapeutically effective amount of a compound having the general formula:

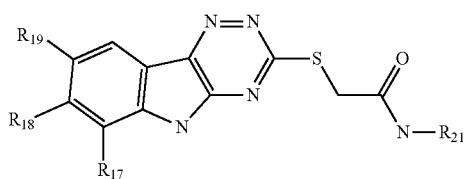

wherein $R_{17}$, $R_{18}$, $R_{19}$, and $R_{21}$ can each individually represent a substituent selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, $(CH_2)_n OR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, C=O, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group and R' represents hydrogen, an alkyl group, an alkenyl group, an alkynyl group, an aryl group, an alkaryl group, an aralkyl group, an alkyloxy group, a cyano, or an isocyano group), and a pharmaceutically acceptable salt thereof, the leukemia characterized by an SHP-2 activating E76K mutation.

2. The composition of claim 1, wherein $R_{17}$, $R_{18}$, and $R_{19}$, can each represent H or a lower alkyl group and $R_{21}$ is selected from the group consisting of H, F, Cl, Br, I, a lower alkyl group, an alkylene group, an alkenyl group, an alkynyl group, an alkoxy group, an aryl group, an aryloxy group, an alkaryl group, and an aralkyl group.

3. The method of claim 1, the compound being selected from the group consisting of:

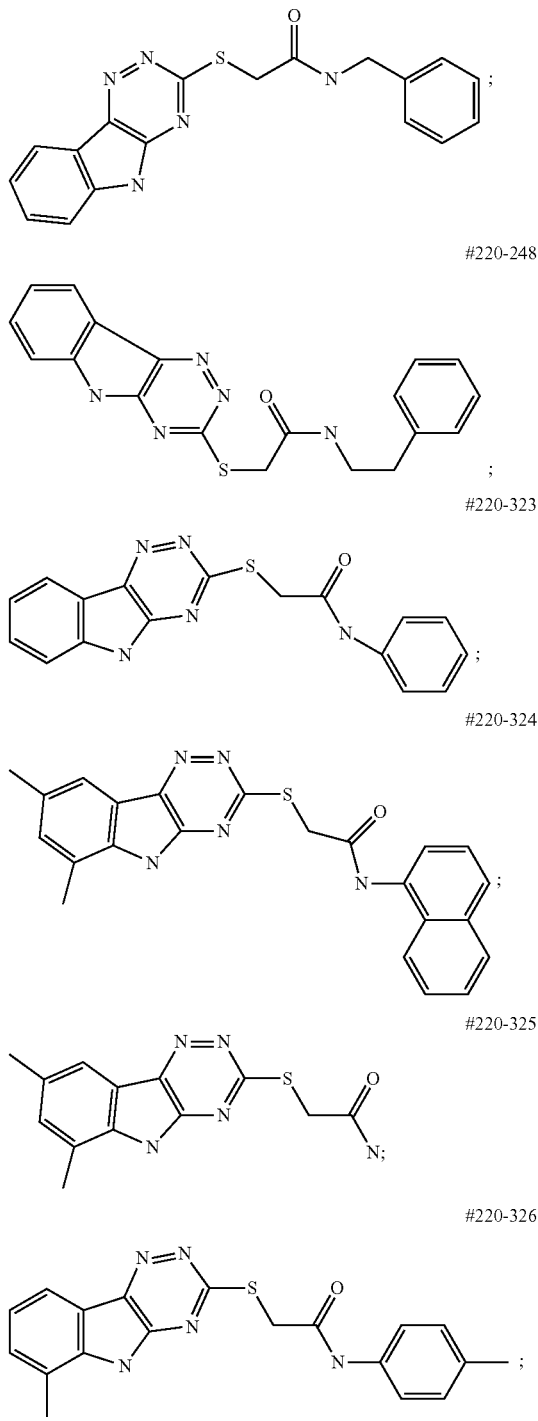

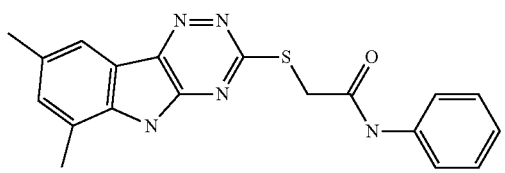
220-328
and a pharmaceutically acceptable salt thereof.
4. The method of claim 1, the compound having following formula:
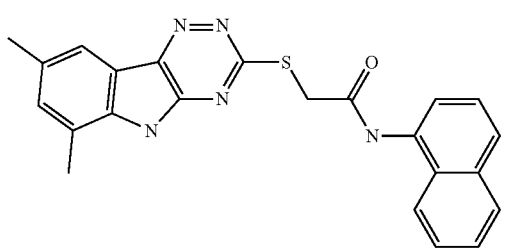
220-324
or a pharmaceutically acceptable salt thereof.
5. The method of claim 1, wherein the leukemia is juvenile myelomonocytic leukemia (JMML).
* * * * *